United States Patent
Sun et al.

(10) Patent No.: US 12,091,676 B2
(45) Date of Patent: Sep. 17, 2024

(54) METHOD FOR PREPARING NON-HUMAN PRIMATE SOMATIC CELL CLONED ANIMAL

(71) Applicant: CENTER FOR EXCELLENCE IN BRAIN SCIENCE AND INTELLIGENCE TECHNOLOGY, CHINESE ACADEMY OF SCIENCES, Shanghai (CN)

(72) Inventors: Qiang Sun, Shanghai (CN); Zhen Liu, Shanghai (CN); Hongjun Zhang, Shanghai (CN); Yijun Cai, Shanghai (CN); Zhaodi Liao, Shanghai (CN); Yuting Xu, Shanghai (CN); Yan Wang, Shanghai (CN); Yanhong Nie, Shanghai (CN)

(73) Assignee: CENTER FOR EXCELLENCE IN BRAIN SCIENCE AND INTELLIGENCE TECHNOLOGY, CHINESE ACADEMY OF SCIENCES, Shanghai (CN)

( * ) Notice: Subject to any disclaimer, the term of this patent is extended or adjusted under 35 U.S.C. 154(b) by 1012 days.

(21) Appl. No.: 16/963,074

(22) PCT Filed: Dec. 25, 2018

(86) PCT No.: PCT/CN2018/123507
§ 371 (c)(1),
(2) Date: Sep. 29, 2020

(87) PCT Pub. No.: WO2019/141052
PCT Pub. Date: Jul. 25, 2019

(65) Prior Publication Data
US 2021/0017543 A1    Jan. 21, 2021

(30) Foreign Application Priority Data
Jan. 17, 2018   (CN) .......................... 201810044287.6

(51) Int. Cl.
*C12N 15/877*   (2010.01)
*A01K 67/0273*  (2024.01)
*C12N 5/073*    (2010.01)
*C12N 5/075*    (2010.01)

(52) U.S. Cl.
CPC ...... *C12N 15/8776* (2013.01); *A01K 67/0273* (2013.01); *C12N 5/0604* (2013.01); *C12N 5/0609* (2013.01); *A01K 2207/10* (2013.01); *A01K 2227/106* (2013.01); *C12N 2510/00* (2013.01)

(58) Field of Classification Search
CPC ............ C12N 15/8776; A01K 67/0273; A01K 2207/10; A01K 2227/106; A01K 2207/05
See application file for complete search history.

(56) References Cited

FOREIGN PATENT DOCUMENTS

| CN | 1814750 A | 8/2006 |
|---|---|---|
| CN | 105543230 A | 5/2016 |

OTHER PUBLICATIONS

Liu et al, Cell, 2018, 172:881-887.*
Matoba (2014, Cell, 159:884-895).*
Chung (Cell Stem Cell 14, 777-780).*
Heng et al (2005a, Cell Tissue Res, 321:147-150.*
Heng, 2005b, Biomedicine and Pharmacotherapy, 59:132-134.*
Bosnali, 2008, Biol Chem, 389:851-861.*
Nakamura, 2016, Nature, 537:57-62.*
Phillips (2014, American Journal of Primatology, 76:801-827).*
Tachibana (Cell 153, 1228-1238, Jun. 6, 2013).*
Sparman (Int J Dev Biol. 2010 ; 54(11-12): 1671-1678).*
Yamada (2017, Nature, 510:532-536).*
English Translation of the International Search Report mailed Feb. 21, 2019 corresponding to PCT/CN2018/123507 filed Dec. 25, 2018; 3 pages.
English Translation of the Written Opinion of the International Searching Authority mailed Feb. 21, 2019 corresponding to PCT/CN2018/123507 filed Dec. 25, 2018; 5 pages.

\* cited by examiner

*Primary Examiner* — Valarie E Bertoglio
(74) *Attorney, Agent, or Firm* — Mintz Levin Cohn Ferris Glovsky and Popeo, P.C.

(57) ABSTRACT

Provided for the first time in the present invention is a method for preparing a non-human primate somatic cell cloned animal, which method specifically comprises the steps of: (i) providing a reconstructed egg, wherein the egg comes from the non-human primate (ii) activating the reconstructed egg to form an activated reconstructed egg or activated reconstructed embryo formed by the reconstructed egg; (iii) reprogramming (a) the activated reconstructed egg or (b) embryonic cells of the activated reconstructed embryo to obtain a reprogrammed reconstructed egg or reprogrammed reconstructed embryo; and (iv) regenerating the reprogrammed reconstructed egg or reprogrammed reconstructed embryo to obtain the non-human primate somatic cell cloned animal. The method of the present invention can significantly improve the developmental capacity of nucleus-transplanted embryos in non-human primates (such as monkeys).

4 Claims, 9 Drawing Sheets
Specification includes a Sequence Listing.

A

| Monkey/Donor cell | D2S1333 | D4S2365 | D12S364 |
|---|---|---|---|
| Deceased cloned monkey infant A | 289/296 | 273/281 | 126/130 |
| Oocyte and cumulus donor of A (#497) | 289/296 | 273/281 | 126/130 |
| Surrogate monkey of A (#2) | 313/313 | 277/277 | 113/124 |
| Deceased cloned monkey infant B | 286/288 | 285/288 | 126/132 |
| Oocyte and cumulus donor of B (#358) | 286/288 | 285/288 | 126/132 |
| Surrogate monkey of B (#128) | 288/292 | 277/281 | 103/103 |

B

C

SEQUENCE LISTING

<160> NUMBER OF SEQ ID NOS: 2

<210> SEQ ID NO 1
<211> LENGTH: 49
<212> TYPE: DNA
<213> ORGANISM: artificial sequence
<220> FEATURE:
<223> OTHER INFORMATION: primer

<400> SEQUENCE: 1
ttaatacgac tcactatagg gatggaaact atgaagtcta aggccaact                49

<210> SEQ ID NO 2
<211> LENGTH: 26
<212> TYPE: DNA
<213> ORGANISM: artificial sequence
<220> FEATURE:
<223> OTHER INFORMATION: primer

<400> SEQUENCE: 2
atataaagac agcccgtgga cttagg                                        26

METHOD FOR PREPARING NON-HUMAN PRIMATE SOMATIC CELL CLONED ANIMAL

REFERENCE TO A "SEQUENCE LISTING,"

The Sequence Listing.txt, created on Sep. 9, 2020 (700 bytes in size), machine format IBM-PC, MS-Windows operating system, is hereby incorporated by reference in its entirety for all purposes.

TECHNICAL FIELD

The present invention relates to the technical field of mammal reproduction, in particular to a method for preparing non-human primate somatic cell cloned animals.

BACKGROUND

Because the brain structure and functional activities of non-human primates are similar to humans in evolution, they are highly similar to humans in many aspects. Compared with other experimental animals, non-human primates have unique advantages in solving human problems, especially brain-related problems: in addition to being a good key laboratory animal for studying the normal brain advanced functions of the human brain, they are also good model animals for studying the mechanism and treatment method of brain diseases. China has a very rich resource of non-human primates. In order to make full use of non-human primates to study brain diseases and the normal advanced functions of the human brain, it is necessary to use transgenic technology to construct a variety of tool models such as non-human primate brain disease models and optogenetics models.

At present, the most commonly used methods for obtaining non-human primate genetically modified animal models are methods through lentivirus infection of oocytes and editable nucleases (CRISPR-Cas9, etc.). In particular, the rapid development of gene editing technology represented by CRISPR-Cas9 has made it easy for scientists to edit genes in non-human primates. Even so, there are still many key problems that have not been resolved in the construction of non-human primate transgenic animal models using existing transgenic technology. For example, firstly, whether using lentivirus to infect oocytes to obtain transgenic animals or using editable nuclease technology to obtain gene knockout animals, chimera is common in the first generation (F0) animal models, which makes the first generation animal models obtained by this method not suitable for scientific research. F1 generation animal models can be obtained in traditional rodents such as rats and mice without chimera through passage, but for non-human primate models, it generally takes about 5 years to obtain F1 generation animal models. Secondly, for non-human primate models carrying complex genetic modifications (conditional knockout or gene knock-in), at present, the methods of introducing site-specific DNA double-strand breaks through embryonic injection of editable nucleases and simultaneous injection of homologous fragments leading to site-specific insertion of foreign fragments are very inefficient at the mammalian level, and it has not been reported successfully at the level of non-human primates. Thirdly, whether it is drug screening or mechanism research, at present, the most commonly used rodent model is preferably inbred line, which can minimize genetic background differences and ensure the rigorous and accurate experimental results. Rats and mice can achieve consistent genetic background through continuous inbred, but for non-human primates with a long sexual maturity cycle, it is definitely unrealistic to achieve genetic background consistency through inbred. In other words, due to the existence of the above three key issues, although there is an urgent need for non-human primate gene-modified animal models, non-human primate gene-modified animal models have not been widely used in scientific research.

At present, success in cloned monkeys derived from somatic cells have not been reported. The main reasons why this project has not been successful are as follows. Firstly, the technical requirements are high, and the primate nuclear transfer technology is much more difficult to operate than other mammals that have been successful. Secondly, the development efficiency of cloned embryos is low. At present, the development efficiency of cloned embryos of monkey somatic cells is far lower than that of other mammals.

Therefore, there is an urgent need to successfully construct a non-human primate cloned animal derived from somatic cells.

SUMMARY OF THE INVENTION

The purpose of the present invention is to provide a non-human primate cloned animal derived from somatic cells.

Another object of the present invention is to provide a method for optimizing the operation process of non-human primate somatic cell nuclear transfer and improving the efficiency of non-human primate somatic cell nuclear transfer and using the optimized operation and method, to obtain a healthy and viable cloned monkey derived from somatic cell nuclear transfer.

In a first aspect of the present invention, it provides a method for preparing a non-human primate somatic cell cloned animal, comprising the steps:
  (i) providing a reconstructed oocyte, which is from the non-human primate;
  (ii) performing activation treatment on the reconstructed oocyte to obtain an activated reconstructed oocyte or an activated reconstructed embryo formed from the reconstructed oocyte, wherein the reconstructed embryo is in the 2-cell stage, 4 cell stage or 8-cell stage;
  (iii) reprogramming the embryonic cell of (a) the activated reconstructed oocyte or (b) the activated reconstructed embryo to obtain a reprogrammed reconstructed oocyte or a reprogrammed reconstructed embryo; and
  (iv) regenerating the reprogrammed reconstructed oocyte or reprogrammed reconstructed embryo to obtain a non-human primate somatic cell cloned animal.

In another preferred embodiment, in the step (iii), the reprogramming treatment is performed with a reprogramming activator.

In another preferred embodiment, the reprogramming activator is selected from the group consisting of:
  (a1) Kdm4d protein;
  (a2) mRNA encoding Kdm4d protein;
  (a3) DNA encoding Kdm4d protein; and
  (a4) any combination of the above (a1), (a2), (a3).

In another preferred embodiment, the reprogramming activator comprises a reprogramming activator selected from the group consisting of:
  (a1) Kdm4d protein;
  (a2) mRNA encoding Kdm4d protein;
  (a3) DNA encoding Kdm4d protein; and
  (a4) any combination of the above (a1), (a2), (a3).

In another preferred embodiment, the reprogramming activator further comprises a reprogramming activator selected from the group consisting of:
(b1) Kdm4a protein;
(b2) mRNA encoding Kdm4a protein;
(b3) DNA encoding Kdm4a protein; and
(b4) any combination of the above (b1), (b2), (b3).

In another preferred embodiment, the reprogramming activator further comprises a reprogramming activator selected from the group consisting of:
(c1) Kdm4b protein;
(c2) mRNA encoding Kdm4b protein;
(c3) DNA encoding Kdm4b protein; and
(c4) any combination of the above (c1), (c2) and (c3).

In another preferred embodiment, the reconstructed oocyte or the reconstructed embryo is a reconstructed oocyte or reconstructed embryo that has not undergone genetic engineering operations or has undergone genetic engineering operations.

In another preferred embodiment, the genetic engineering operation comprises ZFN (zinc-finger nucleases), TALEN or Crispr technology.

In another preferred embodiment, the reconstructed oocyte or reconstructed embryo that has undergone genetic engineering operations comprises the reconstructed oocyte or reconstructed embryo in which the BMAL1 gene has been knocked out.

In another preferred embodiment, the reprogramming treatment comprises: injecting mRNA encoding Kdm4d protein into the reconstructed oocyte or embryonic cell of the reconstructed embryo.

In another preferred embodiment, the reprogramming treatment comprises: injecting mRNA encoding one or more of Kdm4a, Kdm4b or Kdm4d protein into the reconstructed oocyte or embryonic cell of the reconstructed embryo.

In another preferred embodiment, $10^2$-$10^8$ (preferably $10^4$-$10^6$) copies/cell of mRNA encoding Kdm4d protein are injected into the reconstructed oocyte or the embryonic cell.

In another preferred embodiment, $10^2$-$10^8$ (preferably $10^4$-$10^6$) copies/cell of mRNA encoding one or more of Kdm4a, Kdm4b or Kdm4d protein are injected into the reconstructed oocyte or the embryonic cell.

In another preferred embodiment, the reconstructed embryo is in the 4-cell stage or the 8-cell stage.

In another preferred embodiment, the mRNA encoding Kdm4d is in a solution, and the concentration of the mRNA is 10-6000 ng/μl (preferably, 50-4000 ng/μl, more preferably, 80-3000 ng/μl).

In another preferred embodiment, the mRNA encoding Kdm4a or Kdm4b is in a solution, and the concentration of the mRNA is 10-6000 ng/μl (preferably, 50-4000 ng/μl, more preferably, 80-3000 ng/μl).

In another preferred embodiment, the regeneration is performed in the uterus of a non-human primate surrogate animal.

In another preferred embodiment, the species of the surrogate animal is the same as the species of the reconstructed oocyte.

In another preferred embodiment, the regeneration is performed in an artificial uterus.

In another preferred embodiment, in the step (ii) of the method, an activated reconstructed embryo is obtained; and in the step (iii), reprogramming treatment is performed on the reconstructed embryo.

In another preferred embodiment, in the step (iv) of the method, the reprogrammed reconstructed embryo is regenerated to obtain a non-human primate somatic cell cloned animal.

In another preferred embodiment, the step (iv) includes:
(iv1) culturing the reprogrammed reconstructed oocyte in vitro or in vivo to form a reconstructed embryo; and
(iv2) transplanting the reconstructed embryo into the oviduct of a non-human primate, thereby obtaining a somatic cloned animal of the non-human primate.

In another preferred embodiment, the transplantation is a non-invasive transplantation (that is, without causing any trauma).

In another preferred embodiment, the method is non-therapeutic and non-diagnostic.

In another preferred embodiment, the reconstructed oocyte is prepared by an in vitro method comprising the following steps:
(a) providing an enucleated non-human primate donor oocyte and a non-human primate somatic cell with a donor nucleus;
(b) injecting the non-human primate somatic cell with a donor nucleus directly into the enucleated donor oocyte by microinjection to form the reconstructed oocyte.

In another preferred embodiment, the somatic cell is selected from the group consisting of a fibroblast, a cumulus cell, an embryonic stem cell, a spermatogonium, a sertoli cell, a mesenchymal stem cell, a skin cell, a breast cell, an oviductal cell, an ear cell, an ovarian cell, an epithelial cell, an endothelial cell, a muscle cell, a nerve cell, an osteoblast, and a combination thereof.

In another preferred embodiment, in the step (ii), the activation treatment is performed with an activation treatment agent.

In another preferred embodiment, the activation condition of the activation treatment is as follows:
at 37° C. and 5% $CO_2$, using ionomycin for 2-6 minutes, 6-DMAP for 3-6 hours, and TSA for 5-15 hours.

In another preferred embodiment, the activation treatment agent is selected from the group consisting of: calcium ion activator, histone deacetylase inhibitor, 6-DMAP, Cycloheximide (CHX), and a combination thereof.

In another preferred embodiment, the histone deacetylase inhibitor is selected from the group consisting of: TSA, scriptaid, and a combination thereof.

In another preferred embodiment, the concentration of the activation treatment agent is 0.1 nM-100 mM; preferably, 1 nM-50 mM. For example, for ionomycin, the concentration is 0.5 mM-30 mM, preferably 0.8 mM-15 mM, more preferably 1-10 mM.

In another preferred embodiment, in the activation treatment agent, the concentration of the histone acetylase inhibitor (TSA) is 0.5-80 nM, preferably, 1-50 nM, more preferably, 3-30 nM.

In another preferred embodiment, the step (ii) includes one or more features selected from the group consisting of:
(i) activated in a calcium ion activator for 0.5 min-1 h, preferably, 1 min-30 min, more preferably, 2 min-10 min;
(ii) activated in TSA and 6-DMAP for 0.5 h-20 h, preferably 0.8 h-10 h, more preferably, 1 h-8 h;
(iii) activated in TSA for 0.5 h-24 h, preferably 0.8 h-15 h, more preferably 10-12 h.

In another preferred embodiment, in the step (iii), the activated reconstructed oocyte is reactivated for 2-10 hours, preferably, 3-7 hours.

In a second aspect of the present invention, it provides a kit, comprising:
- (a) a first container containing a reprogramming activator, wherein the reprogramming activator comprises a reprogramming activator selected from the group consisting of:
  - (a1) Kdm4d protein;
  - (a2) mRNA encoding Kdm4d protein;
  - (a3) DNA encoding Kdm4d protein;
  - (a4) any combination of the above (a1), (a2), (a3);
- (b) a second container containing an activation treatment agent; and
- (c) labels or instructions.

In another preferred embodiment, the reprogramming activator further includes a reprogramming activator selected from the group consisting of:
- (b1) Kdm4a protein;
- (b2) mRNA encoding Kdm4a protein;
- (b3) DNA encoding Kdm4a protein; and
- (b4) any combination of the above (b1), (b2), (b3).

In another preferred embodiment, the reprogramming activator further includes a reprogramming activator selected from the group consisting of:
- (c1) Kdm4b protein;
- (c2) mRNA encoding Kdm4b protein;
- (c3) DNA encoding Kdm4b protein; and
- (c4) any combination of the above (c1), (c2) and (c3).

In another preferred embodiment, the method according to the first aspect of the present invention is described in the labels or instructions.

In a third aspect of the present invention, it provides a use of the kit according to the second aspect of the present invention for preparing a kit for the preparation of a non-human primate somatic cell cloned animal.

In a fourth aspect of the present invention, it provides a non-human primate somatic cell cloned animal, which is prepared by the method according to the first aspect of the present invention.

It should be understood that, within the scope of the present invention, each technical feature of the present invention described above and in the following (as examples) may be combined with each other to form a new or preferred technical solution, which is not listed here due to space limitations.

wherein, A shows the cynomolgus macaques cumulus cells;

B shows the spindle-chromosome complex reformed by the nucleus after cumulus cells fuse with enucleated oocytes;

C and D show that nuclear transfer embryos form a single pronucleus after activation in vitro;

E shows development of embryos activated by conventional conditions and treated with TSA;

F shows blastocysts developed by the embryo treated with TSA and injected with H3K9me3 demethylase Kdm4d mRNA after the conditions optimized.

Figure 7:
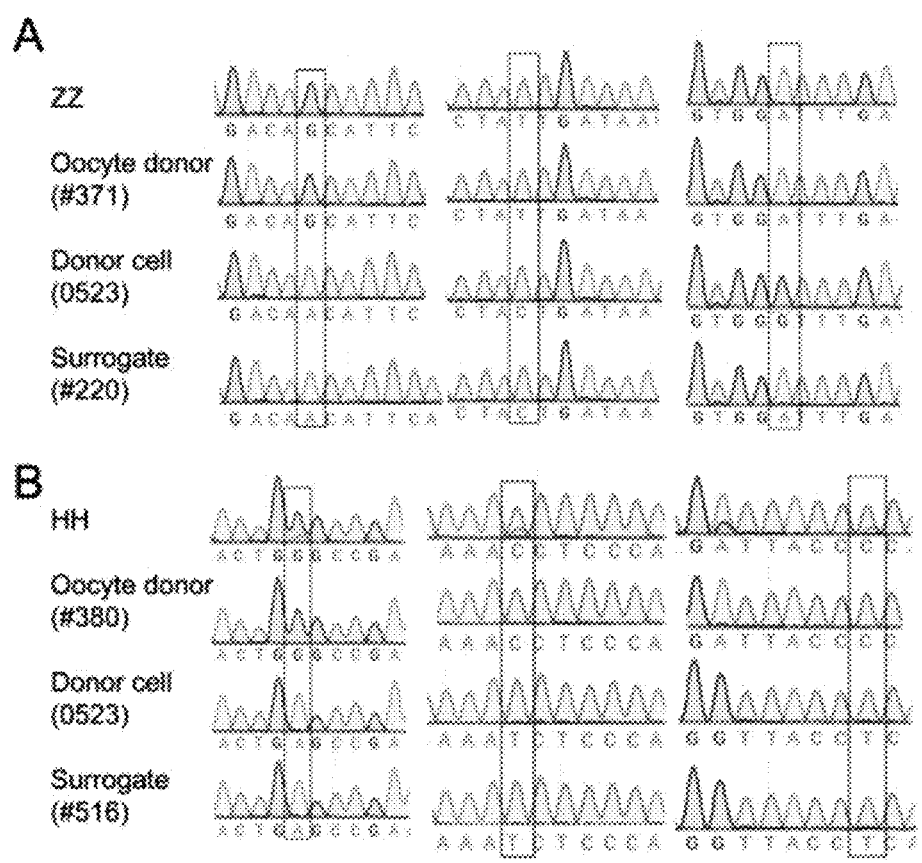

FIG. 7 shows more mitochondrial SNP site analysis of fibroblast nuclear transfer cloned monkey "ZhongZhong" and "HuaHua" (for FIG. 4D).

Figure 8:
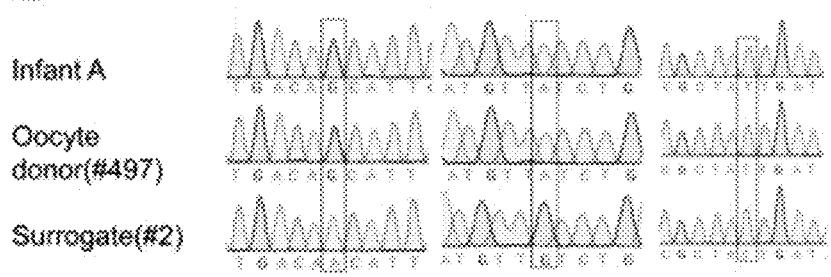
Figure 8:
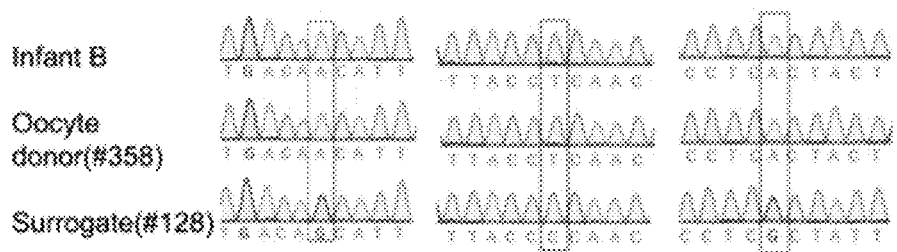

FIG. 8 shows the genetic analysis of cumulus cell somatic cell nuclear transfer cloned monkey "A" and "B";

wherein, A shows the schematic diagram of analysis of three microsatellite sites in two cloned monkey nuclear genomes;

B and C show the analysis of multiple mitochondrial SNP sites in two cloned monkeys.

Figure 9:
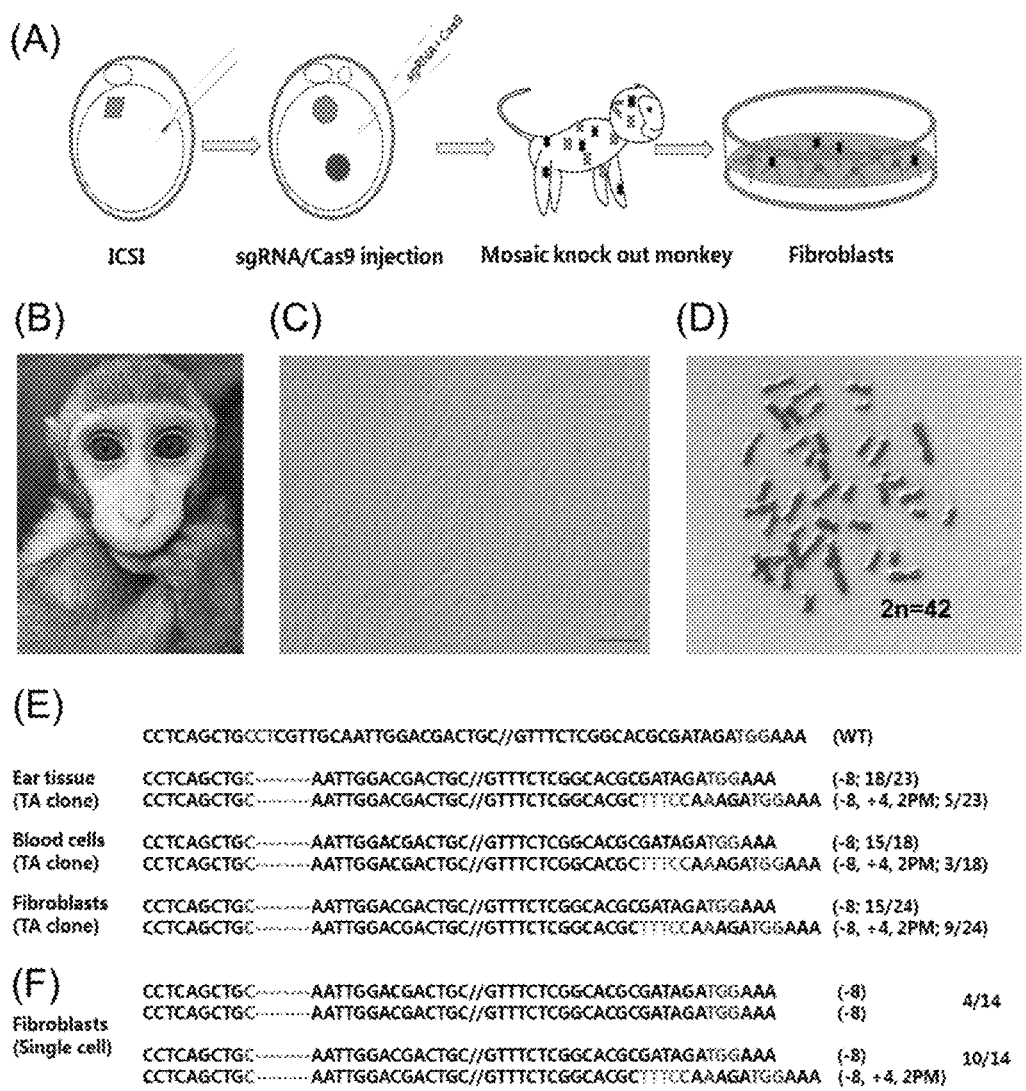

FIG. 9 shows the preparation of BMAL1 gene-edited monkey fibroblasts.

(A) shows the schematic diagram of gene-edited cynomolgus macaques fibroblast preparation. (B) shows the BMAL1 edits monkey A6. (C) shows the skin fiber cells derived from A6 monkey, Bar=200 μm. (D) shows that the karyotype of A6 fibroblasts is normal. (E) shows the genotype analysis of ear tip tissue, blood cells, and fibroblasts in A6 monkey. (F) shows the single cell genotype analysis of A6 fibroblasts.

Figure 10:
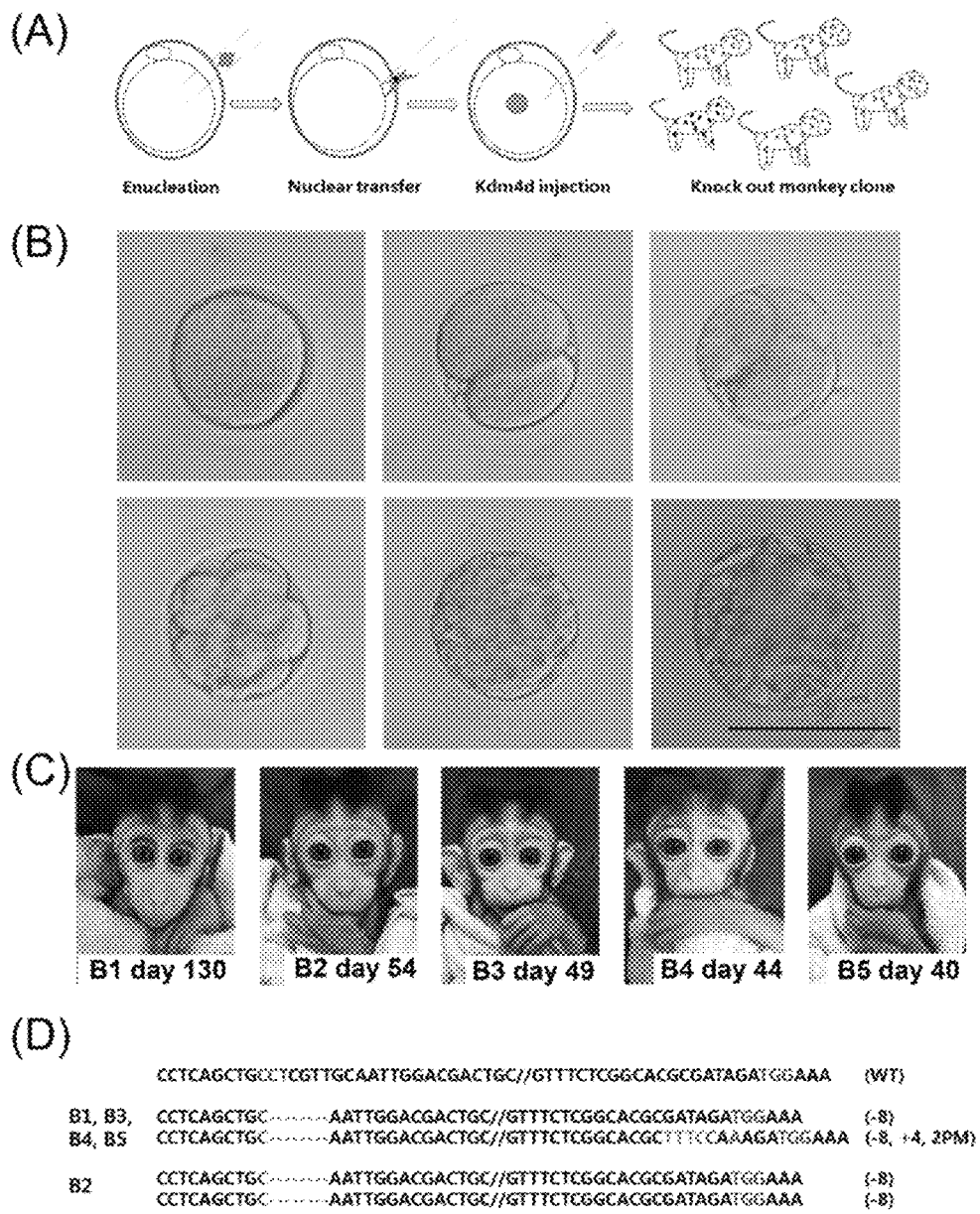

FIG. 10 shows the construction of BMAL1 gene editing cloned monkey.

(A) shows the schematic diagram of construction of BMAL1 gene editing cloned monkey. (B) shows the monkey SCNT embryos at different stages, Bar=120 μm. (C) shows the 5 cloned monkeys performing SCNT from A6 fibroblasts B1-B5. (D) shows the analysis of BMAL1 mutation in 5 cloned monkey ear tissues, wherein 4 monkeys carried heteromutated genes ("−8/−8, +4,2 PM"), and one monkey carried a homozygous mutant gene ("−8/−8") mutation.

Figure 11:
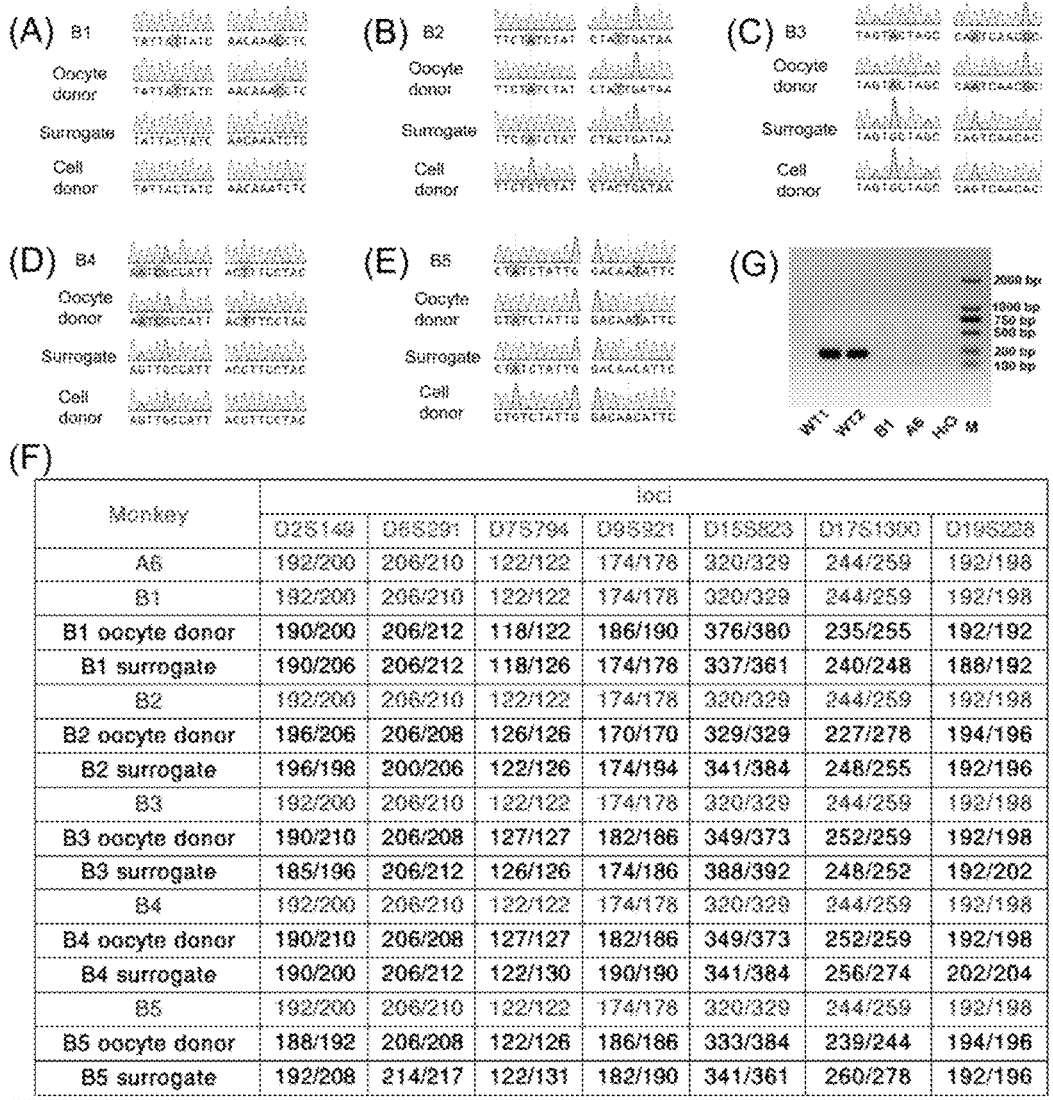

FIG. 11 shows the genotype analysis and expression analysis of cloned monkey BMAL1.

(A-E) show the SNP analysis of B1 to B5, showing that the SNPs of mitochondrial DNA are the same as those of the oocyte donor monkey, but are different from the recipient monkey and the donor fibroblast. (F) shows the short tandem repeats of ear tissues of 5 cloned monkeys (B1-B5) indicating that the nuclear DNA is the same as the donor fibroblasts, but different from the oocyte donor and recipient monkeys. (G) shows the RT-PCR analysis of BMAL1 expression in blood samples of cloned monkey B1 showing that the wild BMAL1 transcript is completely deleted.

DETAILED DESCRIPTION

Through extensive and in-depth research, after a large number of screenings and attempts, the inventors have for the first time unexpectedly developed a method for successfully constructing non-human primate somatic cell cloned animals. Specifically, the inventors used specific reprogramming activators (such as Kdm4d protein, Kdm4d protein-encoding mRNA, Kdm4d protein-encoding DNA, or a combination thereof) to reconstruct oocytes or reconstructed embryos (including gene-edited reconstruct oocytes or reconstructed embryos) for reprogramming treatment, optionally with specific activation treatment agents (such as calcium ion activators (such as ionomycin), histone deacetylase inhibitors (TSA), 6-DMAP, or a combination thereof) to activate the reconstructed oocytes, thereby successfully obtaining a non-human primate somatic cloned animal (such as a monkey) for the first time. On this basis, the inventors have completed the present invention.

Terms

Typically, "reconstructed oocyte" refers to a reconstructed oocyte obtained by injecting a somatic cell (nucleus from a somatic cell) into an enucleated oocyte.

As used herein, the terms "reconstructed embryo" and "reconstructed blasto" are used interchangeably and refer to an embryo developed or differentiated from a reconstructed oocyte, especially an embryo at the 2-16 cell stage. Typically, a reconstructed embryo refers to an embryo divided from a reconstructed oocyte which is obtained by the injection of a somatic cell (nucleus from a somatic cell) into an enucleated oocyte, and all embryos at different cell stages developed from the embryo.

Activation Treatment

As used herein, the term "activation treatment" refers to the activation of the reconstructed oocyte or reconstructed embryo under suitable activation treatment conditions, to promote cell division of the reconstructed oocyte or reconstructed embryo.

In the present invention, the activation treatment can be performed using conventional activation treatment conditions in the art. Typically, an activation treatment agent can be used to activate the treatment at a certain temperature (such as 37±2° C.) for a period of time (such as 0.1-24 hours).

A typical activation condition for activation treatment is at 37° C. and 5% $CO_2$.

In the present invention, the type of activation treatment agent is not particularly limited. Representative examples include (but are not limited to): calcium ion activator, histone deacetylase inhibitor, 6-DMAP, Cycloheximide (CHX), or a combination thereof.

Representative histone deacetylase inhibitors include (but are not limited to): TSA, scriptaid, or a combination thereof.

Representative calcium ion activators include (but are not limited to): ionomycin, calcium ionophore A23187, ethanol, strontium chloride, or a combination thereof.

In another preferred embodiment, the concentration of the activation treatment agent is 0.1 nM-100 mM; preferably, 1 nM-50 mM;

For example, for ionomycin, the concentration is 0.5 mM-30 mM, preferably 0.8 mM-15 mM, more preferably 1-10 mM.

In another preferred embodiment, in the activation treatment agent, the concentration of the calcium ion activator is 0.2-80 μM, preferably, 0.5-50 μM, more preferably, 0.8-20 μM, more preferably, 1-15 μM.

In another preferred embodiment, in the activation treatment agent, the concentration of the histone acetylase inhibitor (TSA) is 0.5-80 nM, preferably, 1-50 nM, more preferably, 3-30 nM.

In another preferred embodiment, in the activation treatment agent, the concentration of the ionomycin is 0.2-80 μM, preferably, 0.5-50 μM, more preferably, 0.8-20 μM, more preferably, 1-15 μM.

In another preferred embodiment, in the activation treatment agent, the concentration of the cycloheximide (CHX) is 0.2-80 μg/ml, preferably, 0.5-50 μg/ml, more preferably, 1-20 μg/ml.

In an embodiment of the present invention, the activation treatment includes: ionomycin treatment for 2-6 minutes, 6-DMAP treatment for 3-6 hours, and TSA treatment for 5-15 hours.

The experimental results of the present invention unexpectedly show that when TSA is used as an activator together with the specific reprogramming treatment agent of the present invention, the success rate of somatic cell cloned animals of non-human primates can be significantly improved.

In the present invention, a preferred activation treatment method includes: the reconstructed embryos that have completed somatic cell injection were treated in 5 ionomycin dissolved in TH3 working solution for a period of time (such as 2-20 minutes, preferably about 5 minutes) (preferably at 37° C. and 5% $CO_2$), and then the embryos were transferred to a liquid solution of 2 mM DMAP and 10 nM TSA dissolved in HECN-9 for a period of time (such as 3-8 hours) (preferably at 37° C. and 5% $CO_2$). Then the embryos were transferred to 10 nM TSA solution dissolved in hamster embryo culture medium 9 (HECM-9) for a period of time (such as 3-8 hours).

Reprogramming Treatment

As used herein, the term "reprogramming treatment" refers to the treatment of reconstructed oocytes or reconstructed embryos, so that the transcription and/or translation status of specific genes in the treated reconstructed oocytes or reconstructed embryos are changed, thereby leading to transcription and translation of genes related to the development of fertilized eggs.

For primates, due to the complexity of the genome, before the present invention, although various reprogramming treatments and/or reactivation treatments on reconstructed oocytes (or reconstructed embryos) have been tried, never been successful. In addition, due to the complexity of the primate genome (for example, little is known about genes related to the development of primate fertilized eggs), before the present invention, it is impossible to predict whether the reconstructed oocytes (or reconstructed embryos) of primates can be successfully and accurately reprogrammed to produce somatic cloned animals.

The inventors have unexpectedly discovered that only one specific substance (i.e., Kdm4d, Kdm4a, or Kdm4b protein or their encoding mRNA or a combination thereof) can be very effective and accurate for targeted reprogramming of reconstructed oocytes. Moreover, the effect of this reprogramming is extremely effective and no observable side effects (such as embryo teratism, miscarriage, etc.) have been found.

A typical reprogramming treatment condition is to perform the reprogramming treatment using an inverted microscope at a temperature that maintains cell viability (such as room temperature, preferably, 25-35° C.).

In the present invention, the type of reprogramming agent is not particularly limited. Representative examples include (but are not limited to): (a1) Kdm4d protein; (a2) mRNA encoding Kdm4d protein; (a3) DNA encoding Kdm4d protein; and (a4) any combination of the above (a1), (a2), (a3).

In another preferred embodiment, $10^2$-$10^8$ (preferably, $10^4$-$10^6$) copies/cell of mRNA encoding Kdm4d protein are injected into the reconstructed oocytes or the embryonic cells.

In another preferred embodiment, the mRNA encoding Kdm4d is in a solution, and the concentration of the mRNA is 10-6000 ng/μl (preferably, 50-4000 ng/μl, more preferably, 80-3000 ng/μl).

In a preferred embodiment, the experimental results of the present invention unexpectedly show that when Kdm4d protein or mRNA encoding Kdm4d protein is used as a reprogramming treatment agent, optionally together with the activation treatment agent of the present invention, the success rate of preparing non-human primate somatic cell cloned animals can be significantly improved.

In a preferred embodiment of the present invention, the method of the present invention includes: after the embryo is activated from 6-DMAP and TSA, it is transferred to HECM-9 containing only TSA, and Kdm4d mRNA injection is performed 1-2 hours later: the embryo is transferred to TH3 working solution containing 5 μg/ml cytochalasin CB, and Piezo Micromainpulator System is used for injection of Kdm4d mRNA into the activated embryo.

Application

Using this method, the cells cultured in vitro can be genetically manipulated first, then the cells that are positive for the transgene are selected, and then the cells can be used as somatic cell nuclear transplantation donor cells to obtain transgenic positive cloned animals. Transgenic offspring are obtained through somatic cell nuclear transfer technology. These cloned animals not only have the same genotype, but also can solve problems such as off-target and chimeric. At the same time, since the first individual can be used for follow-up research, the construction time is basically shortened to the monkey's pregnancy period (about 5.5 months).

Based on the method of the present invention, somatic cell cloned animals of various primates can be effectively prepared. These cloned non-human primates can be used as model animals for scientific research and drug screening.

In addition, in the present invention, the reconstructed oocytes or reconstructed embryos may be or may not be genetically engineered. Representative genetic engineering operations include (but are not limited to): gene editing (such as CRISPR/Cas9-based gene editing), gene recombination, lentiviral transgene, Bacterial Artificial Chromsomes (BAC) transgene, TALEN-based transgene.

In the present invention, the genetic manipulation can be performed before, during, and/or after preparing the reconstructed oocytes. In addition, in the present invention, the genetic manipulation can also be performed before, during, and/or after preparing the reconstructed embryo.

In another preferred embodiment, the reconstructed oocytes, reconstructed embryos, or somatic cloned animals of the present invention have a mutated gene (including knock-in or knock-out genes).

Representative mutations include (but are not limited to):

Genes Knock-In:
(1) Knocking in the green fluorescent protein at AAVS1 site: AAVS1-GFP Knock In.
(2) Knocking in the cre sequence at the AAVS1 site: AAVS1-Cre Knock In.
(3) Knocking in the LSL-CHR2 sequence at the AAVS1 site: AAVS1-LSL-CHR2 Knock In.
(4) Knocking in the light-sensitive ion channel protein CHR2 at CamkIIa site: CamkIIa-CHR2-EYFP Knock In.
(5) Knocking in calcium imaging protein Gcamp6s at CamkIIa site: CamkIIa-Gcamp6s Knock In.
(6) Knocking in cre sequence at CamkIIa site: CamkIIa-Cre Knock In.

(7) Knocking in the light-sensitive ion channel protein CHR2 at Vgat site: Vgat-CHR2-EYFP Knock In.
(8) Knocking in calcium imaging protein Gcamp6s at Vgat site: Vgat-Gcamp6s Knock In.
(9) Knocking in the cre sequence at the Vgat site: Vgat-Cre Knock In.
(10) Knocking in cre sequence at Chat (Choline acetyltransferase) site: Chat-Cre Knock in
(11) Knocking in Chr2 sequence at Chat site: Chat-CHR2-EFYP Knock in
(12) Knocking in Gcamp6s sequence at Chat site: Chat-gcamp6s Knock in
(13) Knocking in the cre sequence at Drd1 (Dopamine receptor D1): Drd1-Cre Knock In
(14) Knocking in Chr2 sequence at Drd1: Drd1-Chr2-EYFP Knock In
(15) Knocking in the cre sequence at Drd2 (Dopamine receptor D2): Drd2-Cre Knock In
(16) Knocking in Chr2 sequence at Drd2: Drd2-Chr2-EYFP Knock In
(17) Knocking in Chr2 sequence at GFAP site: GFAP-CHR2-EFYP Knock in
(18) Knocking in the cre sequence at the GFAP site: GFAP-Cre Knock in
(19) Knocking in gcamp6s sequence at GFAP site: GFAP-gcamp6s Knock in
(20) Knocking in cre sequence at TH (hydroxytryptamine) site: TH-Cre Knock In
(21) Knocking in Chr2 sequence at TH site: TH-Chr2-EYFP Knock In
(22) Knocking in the cre sequence at Nestin site: Nestin-Cre Knock In
(23) Knocking in genes specific to other tissues or cells Point mutations:
(1) SOD1 A4V point mutation
(2) SOD1 H46R point mutation
(3) SOD1 G93A point mutation
(4) Foxp2 T327N+N349S point mutation Genes Knockout:
(1) Cloning the PRRT2 gene knockout with the same genetic background;
(2) Cloning the FMR1 gene knockout with the same genetic background;
(3) Cloning the ASPM gene knockout with the same genetic background;
(4) Cloning the DISC1 gene knockout with consistent genetic background;
(5) Cloning the MKRN3 gene knockout with the same genetic background;
(6) Cloning SNCA gene knockout with consistent genetic background;
(7) Cloning the LRRK2 gene knockout with the same genetic background;
(8) Cloning of GBA gene knockout with consistent genetic background;
(9) Cloning of PRKN gene knockout with consistent genetic background;
(10) Cloning the PINK1 gene knockout with the same genetic background;
(11) Cloning the PARK7 gene knockout with the same genetic background;
(12) Clone the VPS35 gene knockout with the same genetic background;
(13) Cloning the EIF4G1 gene knockout with the same genetic background;
(14) Cloning the Bmal1 gene knockout with the same genetic background;
(15) Cloning the LRRK2+PINK1+PARK7 gene knockout with the same genetic background.

Somatic Cell Nuclear Transfer

As used herein, the term "somatic cell nuclear transfer" is also called somatic cell cloning, which refers to a method of injecting the somatic cell nucleus into the enucleated oocyte, so that the somatic cell nucleus is reprogrammed in the oocyte and reconstructed into a new embryo, thereby obtaining an individual animal.

In the present invention, by genetically modifying the cultured somatic cells in vitro, and then using the genetically modified somatic cells as a nuclear donor to obtain a cloned animal, an animal model carrying a specific genetic modification can be obtained. Using this method, an animal model with complex genetic modification can be obtained, and the obtained F0 generation animal model does not have chimerism, and can be used without passage. In addition, the animal model obtained by using the same cell line has a consistent genetic background. Therefore, the present invention uses somatic cell nuclear transfer technology to construct genetically modified non-human primate models.

The Main Advantages of the Present Invention Include:
(1) The present invention provides for the first time a method for constructing cloned animals of non-human primates derived from somatic cells by using a reprogramming activator (such as Kdm4d protein, mRNA encoding Kdm4d protein, DNA encoding Kdm4d protein, or a combination thereof) and activation treatment agents (such as calcium ion activator (such as ionomycin), histone deacetylase inhibitor (TSA), 6-DMAP, or a combination thereof) on the activation and reprogramming of reconstructed oocytes (including gene editing or not) to obtain non-human primate somatic cloned animals (such as monkeys).
(2) The present invention has discovered for the first time that reprogramming activators (such as H3K9me3 demethylase Kdm4d) can significantly improve the developmental capacity of somatic cell nuclear transfer embryos in nuclear transfer embryos of non-human primates (such as monkeys).
(3) The present invention has discovered for the first time that the injection of 10-6000 ng/µl (preferably 50-4000 ng/µl, more preferably 80-3000 ng/µl) H3K9me3 demethylase Kdm4d into the reconstructed embryos activated by the activation treatment agent at the 1-cell stage can significantly improve the developmental capacity of somatic cell nuclear transfer embryos. More than 50% of embryos have developed to the blastocyst stage, and 3% of blastocysts can develop into mature individuals.
(4) The present invention has discovered for the first time that the efficiency of nuclear transfer using Crispr/Cas9 edited cells as nuclear donors is very high, and the obtained gene-edited non-human primates (such as monkeys) have no off-target phenomenon.

The present invention will be further described below in conjunction with specific embodiments. It should be understood that these embodiments are only used to illustrate the present invention and not to limit the scope of the present invention. The experimental methods that do not indicate specific conditions in the following examples usually follow the conventional conditions or the conditions recommended by the manufacturer. Unless otherwise stated, percentages and parts are calculated by weight.

Unless otherwise specified, the materials or reagents in the examples are all commercially available products.

General Method

1. Separation and Culture of Fetal Monkey Fibroblasts

Aborted fetal monkeys were taken and internal organs, head, limbs, tail and other tissues were removed, and the remaining trunk with scissors were cut to pieces as small as possible, and then put in the cell culture medium containing 1 mg/ml DNase and 0.5 mg/ml type IV collagenase for the digestion (DMEM+10% FBS+antibiotics+non-essential amino acids+glutamine) for four hours (37° C., 5% $CO_2$). The cells obtained by the digestion and separation were transferred to a 10 cm culture dish and cultured until the cells were full of the culture dish, and then the isolated primary cells were digested and resuspended in a cell culture medium containing 10% DMSO and frozen for later use. Before somatic cell nuclear transfer, a tube of cryopreserved primary cells were resuscitated and cultured in a 6-well plate. After the cells were overgrown, they can be used for somatic cell nuclear transfer experiments after continuously cultured for 3 days.

2. Preparation for Isolation of Cumulus Cells from Adult Female Monkeys

The follicular fluid was taken from the cynomolgus/rhesus monkey egg retrieval, centrifuged and washed twice with TH3, and finally resuspended with a small amount of TH3 and placed in a 4° refrigerator for later use.

3. Monkey Superovulation and Oocyte Collection 6-12 years old healthy female cynomolgus monkeys with regular menstruation were selected as oocyte donors. Injection of FSH was started on the third day of menstruation, 25 IU each time, twice a day for 8 consecutive days. 1000 IU of HCG was injected on the eleventh day of menstruation, and laparoscopic egg retrieval was started 36 hours after HCG injection. Through laparoscopic surgery, a vacuum extractor was used to suck follicular fluid with a diameter of 2-8 mm, and the oocytes were selected from the follicular fluid using a glass tube under a stereoscope and transferred to the CMRL-1066 mature medium for later use.

4. Monkey Somatic Cell Nuclear Transfer Procedure

Oocyte denucleation: 15-20 MII stage oocytes were transferred to a glass-bottomed and oil-sealed TH3 working drop containing 5 μm/ml CB, and the position of the oocyte nucleus was observed under the inverted microscope assisted by the spindle imaging system, and the oocyte was fixed with an egg-holding needle and the oocyte nucleus was located at 3 o'clock direction. The Piezo Micromainpulator System was used to drive a flat needle with a diameter of 10 microns to break the zona pellucida, and the oocyte nucleus was removed. After the whole group of oocytes were enucleated, the enucleated oocytes were transferred to HECM-9 medium.

Injection of fibroblasts into enucleated oocytes: 15-20 enucleated oocytes were transferred to an oil-sealed TH3 working drop containing 5 μm/ml CB, and the oocytes were fixed with an egg holding needle, and the polar body was placed at 12 o'clock or 6 o'clock direction. The laser zona pellucida system was used for breaking the zona pellucida to form a narrow slit. An oblique needle with a diameter of 15-18 microns was used for aspirating fibroblasts and transferring the cells to HVJ-E for 10 seconds, and then the cells were removed and injected into the perivitelline space of the enucleated egg cell through the zona pellucida slit, and the somatic cell would fuse into the oocyte in about 10 minutes.

Injection of cumulus cells into enucleated oocytes: 15-20 enucleated oocytes were transferred to an oil-sealed TH3 working drop containing 5 μm/ml CB, and the oocytes were fixed with an egg holding needle, and the polar body was placed at 12 o'clock or at 6 o'clock direction. The laser zona pellucida system was used for breaking the zona pellucida to form a narrow slit. A 10-micron oblique needle was used for aspirating the cumulus cells and transferring the cells to HVJ-E to soak for 10 seconds, then the cells were removed and injected into the 9 o'clock position of the enucleated egg cell through the zona pellucida slit, and the somatic cell would fuse into the oocyte in about 10 minutes.

In vitro activation of nuclear transfer embryos: Embryo activation can be performed 1-1.5 hours after the fusion of somatic cells and enucleated oocytes. The embryos were transferred to TH3 containing 5 μM ionomycin for 5 minutes, then transferred to HECM-9 medium containing 2 mM 6-DMAP and 10 nM TSA for 5 hours, then transferred to HECM-9 containing 10 nM TSA and cultured for 5 hours, and finally transferred to HECM-9 medium for culture.

Kdm4d mRNA injection: 5-6 hours after embryo activation, the activated embryo was transferred to an oil-sealed TH3 working drop containing 5 μg/ml CB, the embryo was fixed with an egg-holding needle, and the Piezo Micromainpulator System was used to drive a flat injection needle with a diameter of 2-3 microns to break the zona pellucida and penetrate deep into the embryo. The embryo cell membrane was broken and 1000 ng/μl of Kdm4d mRNA was injected into the embryo, and each embryo was injected about 10 pl. After the injection, the embryos were transferred to HECM-9 medium and cultured at 37° C. and 5% $CO_2$.

5. Cloned Embryo Culture and Embryo Transfer

Embryo culture: cloned embryos were cultured in HECM-9 medium, and then transferred to HECM-9 medium containing 5% FBS at the 8-cell stage, and the medium was changed every other day until blastocysts were appeared on day 7-8.

Embryo transfer: healthy adult female monkeys in the large follicular phase or ovulatory period were selected for embryo transfer. 3-7 of 2-cell-blastocyst stage embryos were transplanted into the oviduct of a female monkey through minimally invasive surgery.

6. Kdm4d mRNA In Vitro Transcription

The CDS region of the human Kdm4d gene was amplified from the plasmid carrying the Kdm4d gene sequence using primers containing T7 promoters (F: TTAATACGACT-CACTATAGGGATGGAAACTATGAAGTCTAAGGC-CAACT (SEQ ID NO.:1), R: ATATAAA-GACAGCCCGTGGACTTAGG (SEQ ID NO.:2)), and the amplified fragment was purified and recovered, and mMES-SAGE mMACHINE T7 ULTRA kit (Life Technologies, AM1345) was used for in vitro transcription, then the transcription product was purified with MEGA clear kit (Life Technologies, AM1908) and dissolved in RNAse free water.

7. Declaration of Animal Ethics

The use and care of cynomolgus monkeys (*Macaca fascicularis*) are in compliance with the approval document entitled "Gene-modified monkey model passed somatic cell nuclear transfer (ION-2018002) approved by the Animal Committee of the Shanghai Institutes for Biological Sciences, Chinese Academy of Sciences. In this experiment, the monkey used was placed in an air-conditioned environment (temperature: 22±1 degrees Celsius; humidity: 50%±5% RH), 12-hour light/12-hour dark cycle (07:00 to 19:00). All feeds were purchased from Suzhou Anmufei Company, given twice a day, wherein green feeds were mainly fruits and vegetables, supplemented once a day.

8. Fibroblast Culture, Gene Analysis and Karyotype Identification

A small piece of skin from the BMAL1-edited monkey A6 skin anesthetized on the outside of the thigh. The tissue was washed three times with PBS containing penicillin and streptomycin, then cut into small pieces (1-2 mm$^2$), and cultured in a 6 cm culture dish. After 10 days, the fibroblasts grown from the tissue explants were passaged to a 10 cm culture dish, and thereafter, passaged at a ratio of 1:3 every 3 days.

Ear tissues, blood cells and cultured fibroblasts from A6 monkeys were used for genotyping. The primers of the BMAL1 detection site were forward: ACCATCGGCTGCGTACACCTCTAT, reverse: ATTTCAGGTGTGAGCCACTCCACC. PCR products were subjected to TA cloning and sequencing analysis.

Karyotype analysis: A6 fibroblasts grown in a 10 cm culture dish were treated with 100 ng/ml demecolcine for 4-6 hours, then digested with 0.25% trypsin-EDTA, and then treated with 0.075M potassium chloride at 37° C. for 30 minutes. The hypotonic treated cells were fixed in methanol and acetic acid (3:1) for 30 minutes and then dripped. Finally, Giemsa staining and chromosome counting were performed.

9. Superovulation and Embryo Collection

The methods of superovulation and oocyte collection in cynomolgus monkeys were as described above. 25 IU of recombinant human follicle stimulating hormone was injected into the muscle of healthy female macaque twice a day from the 3rd to the 11th day of menstruation. On the night of the 11th day, 1000 IU of human chorionic gonadotropin (hCG) was injected intramuscularly. The next day, the oocytes were collected by laparoscopy and a negative pressure suction system. The collected oocytes were cultured in pre-equilibrated HECM-9 medium. The oocytes in the metaphase of the second meiotic division were selected as SCNT.

10. Somatic Cell Nuclear Transfer, Embryo Culture, Embryo Transfer

The spindle-chromosome complex was quickly removed by a piezo-driven enucleating needle under the Oosight system. A laser was used to make a notch in the zona pellucida of the enucleated oocytes, and then an oblique needle was used to inject HVJ-E-contaminated fibroblasts into the perivitelline space and mediate their fusion. Reconstituted nuclear transfer embryos were activated in TH3 (HEPES-buffered TALP medium, containing 0.3% bovine serum albumin), first treated with TH3 containing 5 mM calcium ionophore for 5 minutes, and then treated in TH3 containing 2 mM 6-dimethylamine for 5 h. Nuclear transfer embryos were treated with 10 nM Trichostatin (TSA) for 10 h, and 10 pl 1000 ng/ml Kdm4d mRNA was injected 6 h after activation.

Embryos were cultured in HECM-9 medium, wherein the incubator conditions were 37 degrees Celsius, 5% carbon dioxide. When the embryo reached the 8-cell stage, it was transferred to HECM-9 medium supplemented with 5% fetal bovine serum, and then the medium was changed every two days until it reached the blastocyst stage. The embryos from the 2 to 8 cell stage of high-quality development were transferred to the oviducts of female monkeys (with ovulation points or corpus luteum) whose menstrual cycles were synchronized.

11. Genetic Analysis of Cloned Monkeys

Genomic DNA was extracted from the ear tissues of cloned monkeys for short tandem repeat (STR) analysis. Site-specific primers containing fluorescent dyes (FAM/HEX/TMR) were used for PCR amplification. The fluorescent dye-labeled STR amplicon was diluted with a mixture of ROX500 and deionized formamide, and then subjected to capillary electrophoresis on the ABI PRISM 3730 genetic analyzer to obtain raw data. As a result, Gene Marker 2.2.0 was used for generating Excel files from the raw data, including size and genotype information, DNA samples and wave diagrams.

Single nucleotide polymorphism (SNP) analysis, mtDNA was also extracted from monkey ear tissue samples. The mtDNA was amplified with specific primers (F: CCACTTCACATCAAACCATCACTT, R: CAAGCAGCGAATACCAGCAAAA), and the PCR products were used for sequencing and SNP analysis.

12. RT-PCR 0.5 ml of blood was collected from each of A6, B1 and two wild-type monkeys, and mRNA was extracted with total RNA TRIzol® Reagent (Invitrogen) kit. Then the total RNA was reverse transcribed into cDNA using PrimeScript™ RT reagent Kit with gDNA Eraser (Perfect Real Time, Takara, Japan) kit. BMAL1 primers (forward primer; 5"-TAACCTCAGCTGCCTCGTTG-3", reverse primer; 5'-TATTCATAACACGACGTGCC-3") were used for amplifying the 201 bp target fragments of wild BMAL1, and then electrophoretic analysis was performed.

Example 1 Establishment and Optimization of the Operation Process of Monkey Nuclear Transfer Technology The nucleus of the oocytes of rats and mice can be clearly distinguished under a normal inverted microscope, and can be easily aspirated and removed with a micromanipulation needle. However, the nucleus of primate oocytes cannot be clearly distinguished under a normal inverted microscope. The previous methods of removing the nucleus of monkey oocytes relied on Hoechst staining followed by fluorescence localization and blind aspiration. The loss of embryos is very large for these two methods and the subsequent development efficiency of embryos can be easily affected. In this study, we used the Oosigt Imaging System based on polarized light, which can clearly distinguish the nucleus of monkey oocytes without affecting the quality of the oocytes. After a lot of training, and after using the spindle imaging system to clearly distinguish the position of the monkey oocyte nucleus, a 10-micron micromanipulator driven by Piezo was used to break the zona pellucida and the monkey oocyte nucleus was sucked out. In order to inject somatic cells into the enucleated oocytes, laser zona pellucida system was used to assist somatic cell injection, and the inactivated Sendai virus was used to induce the fusion of fetal monkey somatic cells and enucleated oocytes. After the fusion, the somatic cell nucleus agglutinated into the shape of the oocyte nucleus. (FIG. 1A-H, FIG. 5 A, B)

Figure 2:
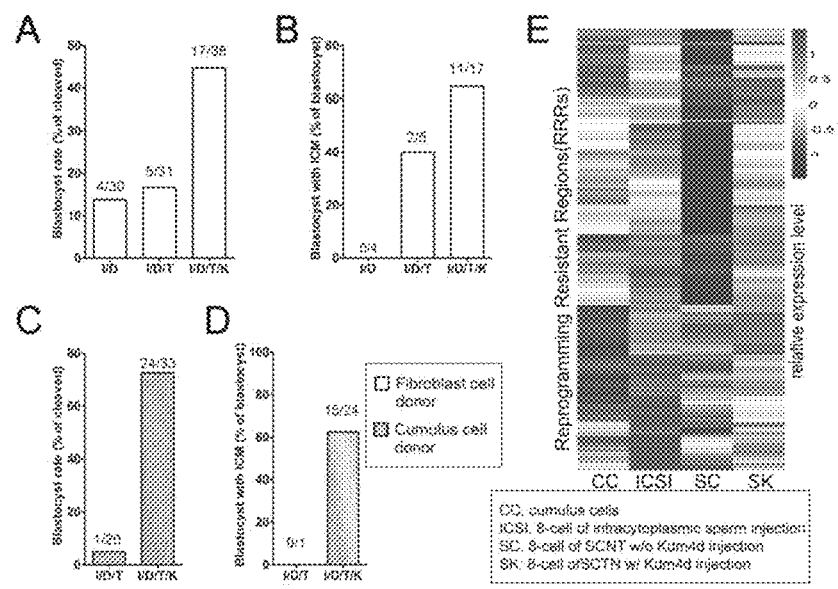
FIG. 2 shows the statistics of efficiencies using fetal monkey fibroblasts and adult monkey cumulus cells as nuclear donors under different conditions;
- wherein, A shows the development statistics of embryonic blastocysts under normal activation conditions, treatment with histone deacetylase inhibitor TSA, injection with TSA plus H3K9me3 demethylase Kdm4d;
- B shows the statistics of high-quality blastocyst development of fibroblast nuclear transfer embryos under three conditions: normal activation conditions, treatment with histone deacetylase inhibitor TSA, injection with TSA plus H3K9me3 demethylase Kdm4d;
- C shows the statistics of blastocyst development of cumulus cell nuclear transfer embryos under the conditions of treatment with histone deacetylase inhibitor TSA and injection with TSA plus H3K9me3 demethylase Kdm4d;
- D shows the statistics of high-quality blastocyst development of cumulus cell nuclear transfer embryos under the two conditions of treatment with histone deacetylase inhibitor TSA and injection with TSA plus H3K9me3 demethylase Kdm4d;
- E shows the transcriptome level verification on the effect of H3K9me3 demethylase Kdm4d on the enhancement of monkey somatic cell nuclear transfer.
Figure 5:
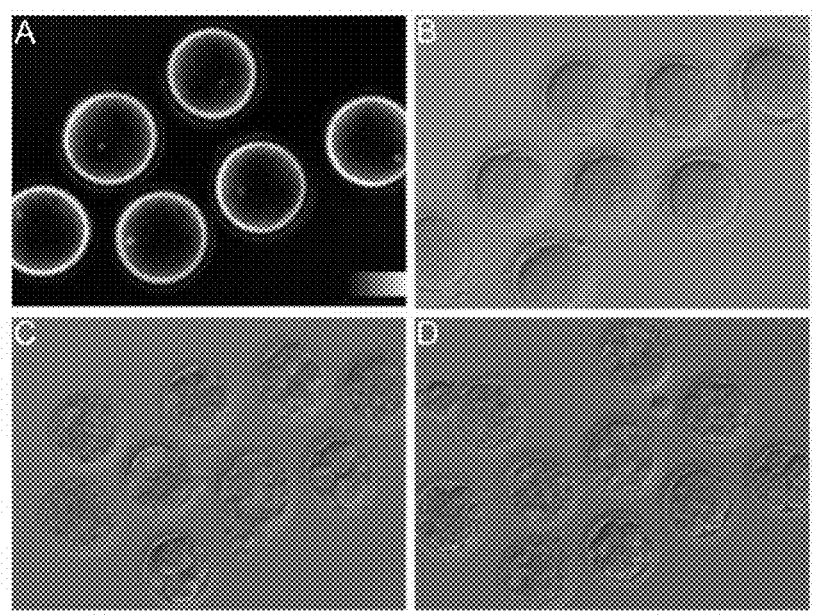
FIG. 5 shows the nuclear transfer of cynomolgus macaques fetal monkey fibroblasts;
- wherein, A shows the spindle-chromosome complex reformed by the nucleus after the fusion of somatic cells and enucleated oocytes (corresponding to FIG. 1G);
- B shows the single pronucleus formed by the nuclear transfer embryos after activation in vitro (corresponding to FIG. 1H);
- C shows the embryo development after activation of conventional conditions;
- D shows the development of embryos activated by conventional conditions and treated with TSA.

Example 2 Study of the Effect of Histone Deacetylation Inhibitor on the Development Efficiency of Monkey Cloned Embryos It is currently believed that one of the reasons for the low efficiency of somatic cell nuclear transfer is that somatic DNA is abnormal in the oocyte reprogramming process, which leads to abnormally increased DNA methylation. Increasing the level of histone acetylation can reduce the level of DNA methylation. In the experiments of the present invention, cynomolgus monkey somatic cell nuclear transferred embryos after normal activation (ionomycin and dimethylaminopyridine 6-DMAP) were cultured in vitro, and it was found that 4/30 embryos developed to the blastocyst stage, but the quality of the four blastocysts were all very poor, and there was no obvious inner cell mass. During and after the activation of the embryo, the histone deacetylase inhibitor TSA (10 nM, 10 h) was added, it was found that 5/31 of the embryos treated with TSA have developed into blastocysts. Although the rate of blastocysts activated by I/D was similar, the quality of blastocysts added to the TSA group was improved, and 2 out of 5 blastocysts had inner cell masses. (FIG. 2 A, B, FIG. 5 C, D)

Example 3 Study on the Influence of Optimized Embryo Activation Conditions on the Development Efficiency of Monkey Cloned Embryos In the study of human cell nuclear transfer cloned embryos, it was found that in addition to using conventional ionomycin and dimethylaminopyridine 6-DMAP to activate embryos, electrical stimulation and puromycin have also been reported to significantly improve the development efficiency of human cloned embryos. In the experiment of optimizing activation conditions of the present invention, using electrical stimulation, ionomycin, dimethylaminopyridine, puromycin, and histone deacetylase inhibitor TSA, it was found that 18 (33.3/%) of 54 cynomolgus monkey somatic cloned embryos had developed into blastocysts, 8 of which had obvious inner cell masses.

Compared with the simple use of ionomycin and dimethylaminopyridine to activate embryos and experimental ionomycin, dimethylaminopyridine and TSA treatment of embryos, the optimized embryo activation conditions can significantly improve the developmental ability of monkey somatic cell nuclear transfer embryos. The embryos constructed by this method were transplanted into the oviduct of female monkey recipients. Although multiple recipients were transplanted, no recipients of monkey somatic cell nuclear transfer pregnancy was obtained.

Example 4 the Effect of Embryo Polymerization on the Efficiency of Non-Human Primate Somatic Cell Nuclear Transfer Abnormal gene expression of somatic cell nuclear transfer embryos is an important reason for its low efficiency, and the expression of Oct4 gene in the inner cell mass (ICM) can be used as an indicator of the quality of the inner cell mass of the cloned embryo. The study of the present invention has shown that the number of cells in the blastocyst stage of mouse cloned embryos was half of the number of normal IVF fetal cells, and in the same way, the number of ICM in mouse cloned embryo blastocysts was about half of that in IVF embryos. The number of ICM in cloned embryos was closely related to the expression of Oct4 gene in ICM. In the monkey somatic cell nuclear transfer embryo polymerization experiment of the present invention, first, a normal cynomolgus monkey embryo obtained by single sperm injection and three somatic cell nuclear transfer embryos gathered together to make them develop together, among the 10 transplant recipients, three pregnant recipients were obtained and two surviving individuals were obtained. However, through genetic analysis, it was found that the only two surviving monkeys are both derived from normal monkey embryos obtained by single sperm injection, while somatic cell nuclear transfer embryos were not involved in the development of individuals. Then 3-4 embryos, all of which were nuclear transfer from monkey somatic cells, were brought to develop together. Although many pregnant recipients were obtained, all of them were aborted early and no surviving individuals was obtained.

Example 5 the Effect of H3K9Me3 Demethylase on the Efficiency of Monkey Somatic Cell Nuclear Transfer In the process of somatic cell nuclear transfer, the abnormality in the reprogramming of somatic cell nucleus by oocytes leads to its low efficiency. Analyzing the sources of reprogramming abnormalities and addressing these abnormalities in a targeted manner may improve the efficiency of somatic cell nuclear transfer.

Figure 1:
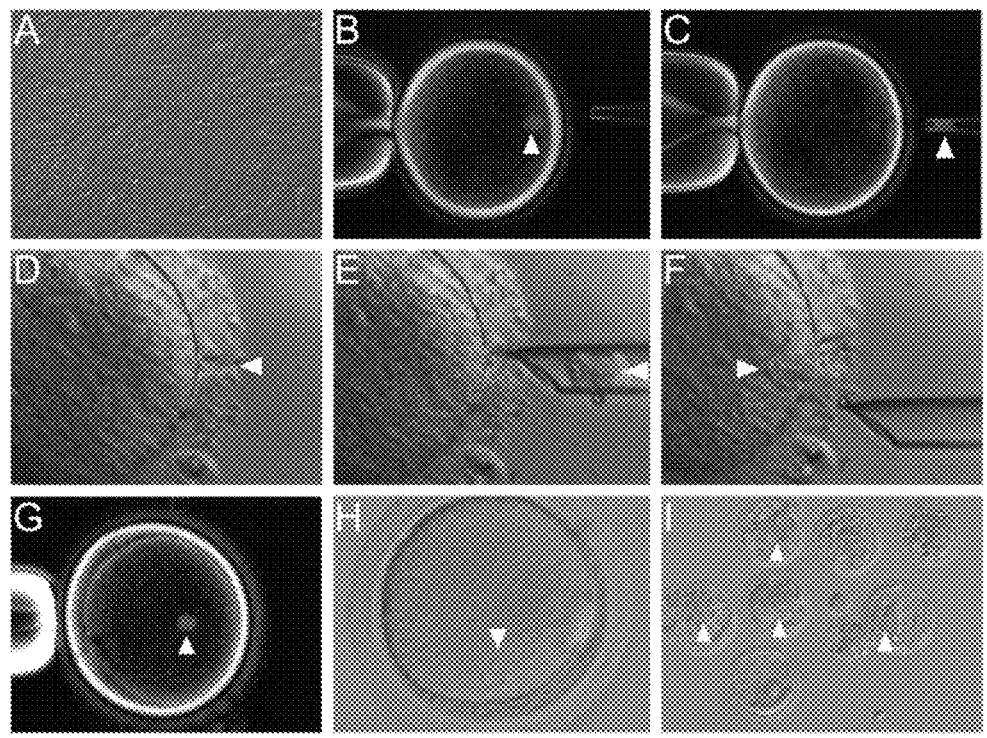
FIG. 1 shows the optimization of the Cynomolgus macaques somatic cell nuclear transfer operation process;
- wherein, A shows the Cynomolgus macaques fetal monkey fibroblasts used as nuclear donors;
- B shows the Cynomolgus macaques oocyte nucleus (spindle-chromosome complex) under the spindle imaging system;
- C shows the removal of Cynomolgus macaques oocyte nucleus using Peizo Micromainpulator System assisted by spindle imaging system;
- D-F show laser assisted in breaking zona pellucida, HVJ-E virus-mediated of the fusion of donor cells and enucleated oocytes;
- G shows the spindle-chromosome complex reformed by the nucleus after the fusion of somatic cells and enucleated oocytes;
- H shows the single pronucleus formed by the nuclear transfer embryos after activation in vitro;
- I shows the blastocysts developed by the embryo treated with TSA and injected with H3K9me3 demethylase Kdm4d mRNA after the conditions optimized.
Figure 6:
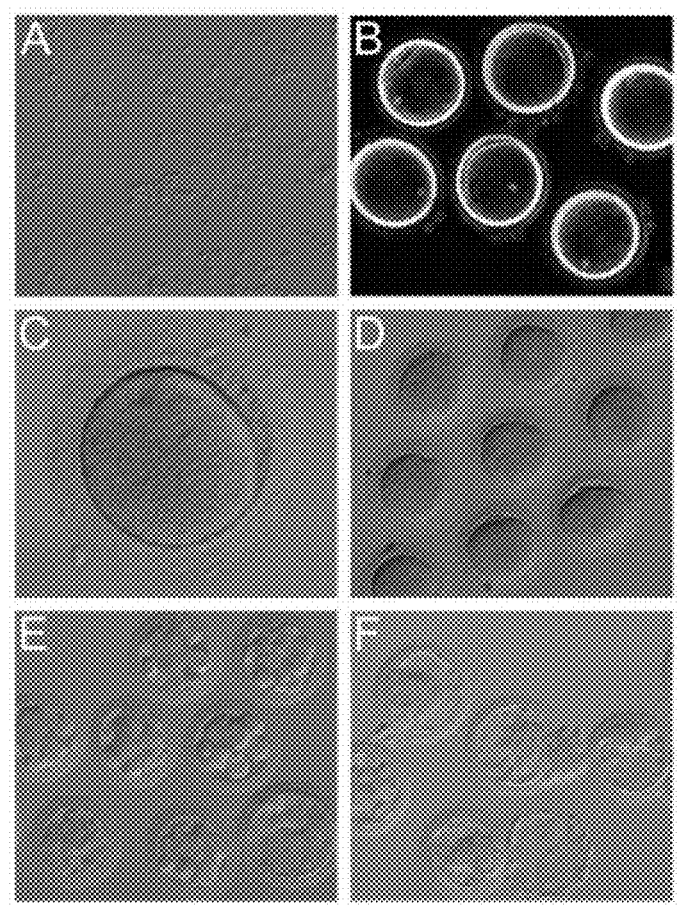
FIG. 6 shows the somatic cell nuclear transfer of cynomolgus macaques cumulus cells and the activation and reprogramming treatment of reconstructed oocyte.

In this example, 38 nuclear transfer embryos were constructed and obtained using fibroblasts from cynomolgus monkey fetal monkeys. After Kdm4d mRNA injection, 17 of them developed to the blastocyst stage, and 11 of them had obvious inner cell masses (FIG. 1I, FIG. 2, A, B). In order to test the effect of Kdm4d in other donor cell nuclear transfer embryos, 33 nuclear transfer embryos were obtained using adult monkey cumulus cells as somatic cell donors. After Kdm4d mRNA injection, 24 of which developed to the blastocyst stage, among them, 15 blastocysts had obvious inner cell masses (FIG. 6, FIG. 2, C, D).

In order to further understand the mechanism of Kdm4d mRNA in enhancing the developmental ability of monkey nuclear transfer embryos, 4-cell and 8-cell stage embryos obtained by normal monkey sperm injection (ICSI) and 8-cell stage embryos with and without Kdm4d injection in monkey nuclear transfer were subjected to transcriptome sequencing. By comparing the transcriptomes of normal ICSI 4-cell stage and 8-cell stage embryos, areas where the expression level of the 8-cell stage was more than 5 times higher than those of the 4-cell stage were screened out, and 3997 transcription activation regions were obtained. Next, the 3997 regions of the transcriptome of the 8-cell nuclear transfer embryos that were not injected with Kdm4d were analyzed, and it was found that 2465 regions were not activated, and these 2465 regions were called reprogramming resistance regions. A comparative analysis of the reprogramming resistance regions in the transcriptome of 8-cell nuclear transfer embryos injected with Kdm4d shows that the expression levels of 2178 regions were significantly increased.

These results indicate that the H3K9me3 demethylase Kdm4d can significantly enhance the developmental ability of somatic cell nuclear transfer embryos in monkey nuclear transfer embryos. (FIG. 2E)

Example 6 the Effect of H3K4Me3 Demethylase on Monkey Somatic Cell Nuclear Transfer Efficiency In this example, the level of embryo in cynomolgus monkey somatic cell nuclear transfer was verified.

A total of 20 monkey somatic cell nuclear transfer embryos were injected and 2 blastocysts were obtained. The blastocyst rate was only 10%, indicating that the H3K4me3 demethylase Kdm5b has no significant effect on improving the efficiency of monkey somatic cell nuclear transfer embryos.

Example 7 Using Cynomolgus Monkey Fetal Monkey Fibroblasts to Obtain Somatic Cell Nuclear Transfer Cloned Monkey In this example, primary fibroblasts from female cynomolgus monkey fetal monkey were used as donor cells for the construction of somatic cell nuclear transfer cloned monkey.

A total of 127 MII stage oocytes were manipulated using the procedures in the general method. After oocyte enucleation, somatic cell injection and embryo activation, 109 single pronuclear embryos were obtained (FIG. 6). These 109 embryos were injected with Kdm4d mRNA, and 79 embryos of 2-cell stage, 2-4 cell stage, 8-cell stage, 8-16-cell stage, or blastocyst stage were transplanted to 21 recipient female monkeys. Through B-ultrasound verification, 6 pregnant female monkeys were successfully obtained. Four of the pregnant female monkeys had gestational sacs and fetuses in their uterus, while the other two pregnant female monkeys had only gestational sacs and no fetuses. Of the four female monkeys with fetuses, two had early miscarriages. Two healthy baby monkeys were obtained through Caesarean from the other two on day 155 (note: 8-16 cell stage for implantation into the surrogate mother) and day 141. The two baby monkeys were named "Zhongzhong" and "Huahua" (Note: 2-4 cell stage for implantation into the surrogate mother). The two baby monkeys have been born for 28 days and 18 days and are in good health. (Picture 3, A-E, Picture 4, A, B)

Example 8 Using Adult Cynomolgus Monkey Cumulus Cells to Obtain Somatic Cell Nuclear Transfer Cloned Monkey In this example, cumulus cells of adult female cynomolgus monkeys were used as nucleus donors to construct cloned monkeys.

Figure 3:
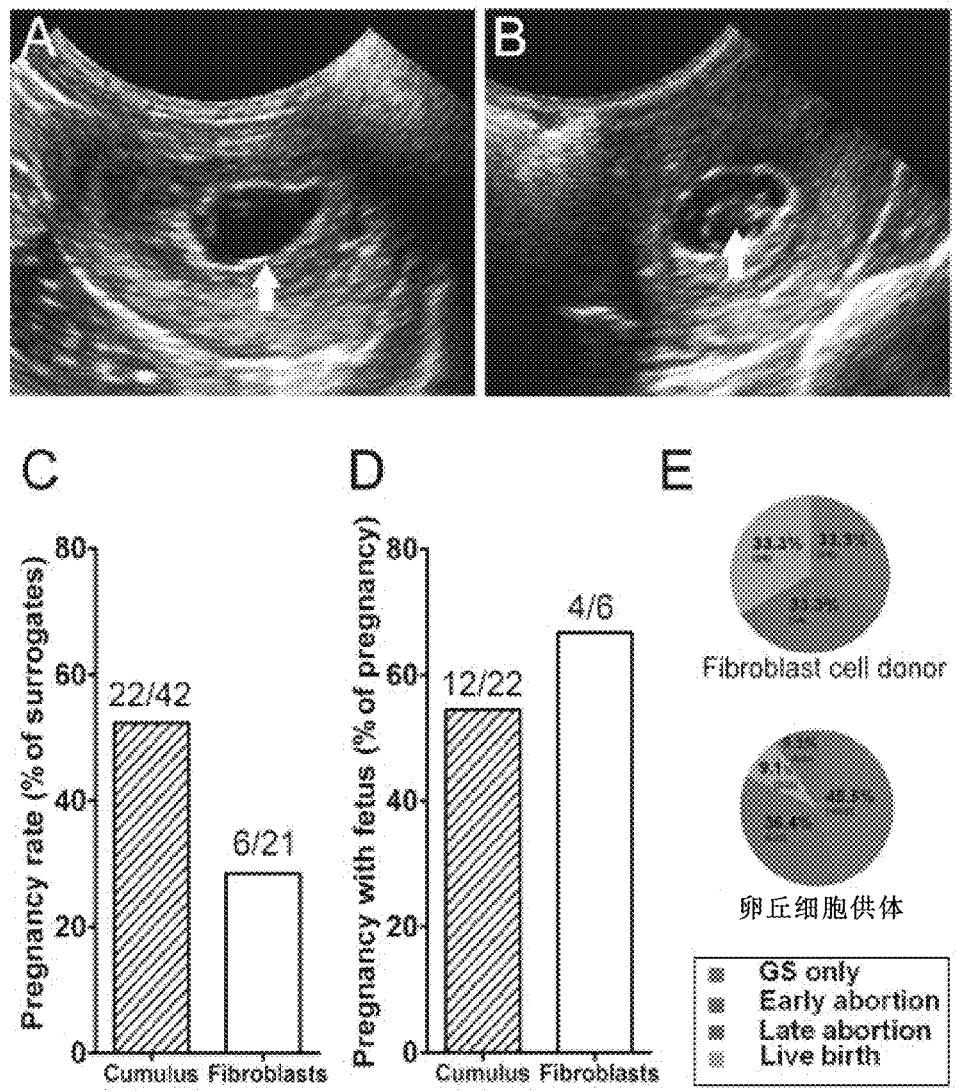
FIG. 3 shows the statistics of the pregnancy rate and fetal development of cynomolgus macaques somatic cell nuclear transfer embryo transfer;
- wherein, A and B show the B-scan of pregnant recipients of nuclear transfer, wherein A recipient only had a gestational sac and no fetus And B recipient had both gestational sac and fetus;
- C and D show the statistics of pregnancy rate of two different cell donors and statistics of the proportion of fetuses carried by pregnant recipients;
- E shows the final development of the pregnant recipient carrying the fetus.

Using the same procedure as in Example 7, a total of 290 oocytes of MII stage were manipulated. After oocyte denucleation, somatic cell injection and embryo activation, 192 single pronucleus embryos were obtained. The 192 embryos were injected with Kdm4d mRNA, and 181 embryos of the 2-cell stage to blastocyst stage were transferred to 42 recipient female monkeys. Through B-ultrasonic verification, 22 pregnant female monkeys were successfully obtained. Among them, 12 pregnant female monkeys had gestational sacs and fetuses in their uterus, while the other 10 pregnant female monkeys had only gestational sacs and no fetuses. Of the 12 female monkeys with fetuses, 8 had early abortions, and two aborted at day 84 and day 94 respectively. In addition, two successfully developed to more than 130 days and got two surviving baby monkeys through caesarean on day 137 and day 135. The two monkeys were named "A" and "B". The baby monkey A was physically retarded and dies of respiratory failure after only 3 hours after birth. Baby monkey B had a normal body shape, and had normal drinking and milk behaviors after birth. (FIG. 3, C, D, E)

Example 9 Using Adult Rhesus Monkey Cumulus Cells to Obtain Somatic Cell Nuclear Transfer Cloned Monkey The two most commonly used non-human primates in scientific research include the cynomolgus monkey and the rhesus monkey. It has been suggested in the research of the above-mentioned embodiment of the present invention that the above-mentioned specific treatment method of the present invention can significantly improve the efficiency of mammalian nuclear transfer.

In this example, in order to further verify the efficiency of H3K9me3 demethylase in non-human primate somatic cell nuclear transfer, the general method was applied to the embryos of rhesus monkey somatic cell nuclear transfer. Results Among the 10 Rhesus monkey somatic cell nuclear transfer embryos injected with H3K9me3 demethylase, 7 of which were in the blastocyst stage. In addition, at present, the pregnant recipient of somatic cell nuclear transfer of rhesus monkeys has been successfully obtained through this embryo transfer, and a cloned rhesus monkey "C" that has grown to 130 days has been obtained. This result suggests that the method of the present invention is also applicable to other non-human primates, especially monkeys.

Figure 4:
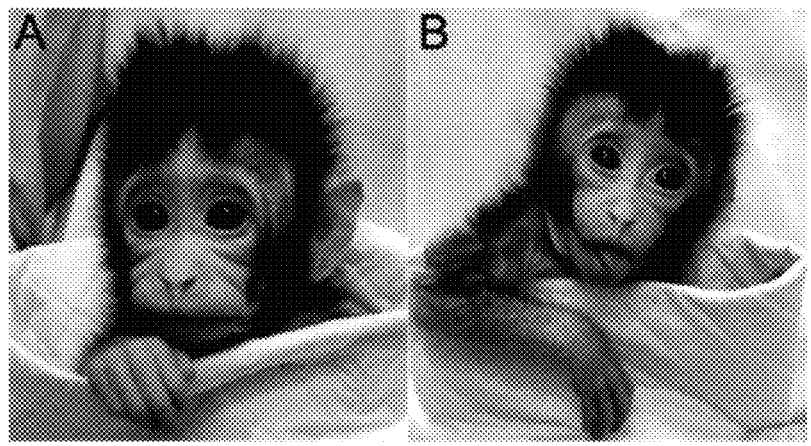
FIG. 4 shows the genetic analysis of somatic cell nuclear transfer cloned monkeys;
- A and B show the two healthy cloned monkeys "ZhongZhong" and "HuaHua" obtained from fibroblasts;
- C shows the schematic diagram of analysis of three microsatellite sites in the two cloned monkey nuclear genomes;
- D and E show the schematic diagrams of mitochondrial SNP analysis of the two cloned monkeys.
Figure 4:
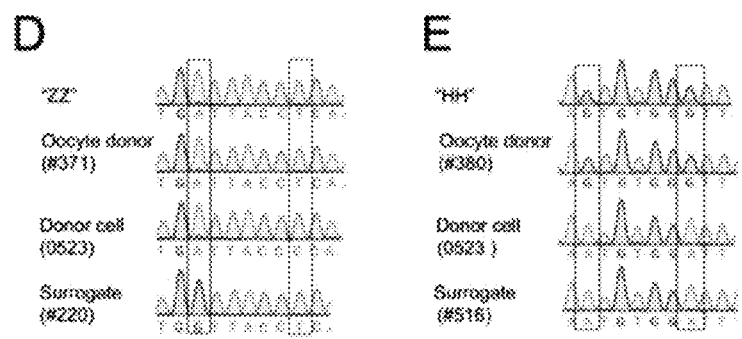

Example 10 Genetic Analysis of Cloned Monkeys Derived from Somatic Cell Nuclear Transfer In order to verify the genetic source of nuclear genomic DNA and mitochondrial DNA of five born monkeys, single nucleotide polymorphism (SNP) and microsatellite sequence analysis (STR) were performed on these four baby monkeys. Through the analysis of 27 microsatellite sites in the baby monkeys "Zhongzhong" and "Huahua", donor cells, their respective surrogate mother monkeys, and their respective egg donor mother monkeys, it is found that the genomes of "Zhongzhong" and "Huahua" are consistent with those of the donor cell, but are inconsistent with the genomes of the surrogate mother monkey and the egg donor mother monkey. SNP analysis of the ND3 gene on the mitochondrial DNA of the baby monkeys "Zhongzhong" and "Huahua", donor cells, their respective surrogate mother monkeys, and their respective egg donor mother monkeys has revealed that the mitochondrial genomes of "Zhongzhong" and "Huahua" are consistent with the mitochondrial genomes of the egg donor monkeys, but are inconsistent with the mitochondrial genomes of the surrogate female monkeys and the egg donor female monkeys. Using the same method, SNP and STR analysis were performed on the monkeys "A" and "B" that died after birth, and it is found that the nuclear genome and mitochondrial genome of baby monkeys "A", "B" and "C" were derived from egg cells and cumulus cell donor monkeys, which is different from the surrogate recipient. These genetic analyses prove that the five baby monkeys are indeed cloned monkeys obtained through cloning technology. (FIG. 4 C, D, E, FIG. 7 and FIG. 8)

By analyzing the 27 STR sites of the four somatic cell cloned monkeys, their oocyte donors, somatic cell donors and pregnant recipients, it was found that the nuclear DNA of the four somatic cell cloned monkeys is indeed from the donor somatic cells.

Example 11 Construction of Non-Human Primate Gene-Modified Animal Model Using Somatic Cell Nuclear Transfer Technology (Taking Cynomolgus Monkey/Rhesus Monkey as an Example)

For the reason why the present invention spent a lot of energy to conquer the use of somatic cell nuclear transfer technology to obtain cloned monkeys, in addition to its own scientific significance, more important is the advantages of this technology in constructing genetically modified animal models. In the present invention, by genetically modifying the cultured somatic cells in vitro, and then using the genetically modified somatic cells as nuclear donors to obtain cloned animals, animal models carrying specific genetic modifications can be obtained. This method can be used to obtain animal models carrying complex genetic modifications, and the obtained F0 generation animal models do not have chimerism, and can be used without passage. In addition, animal models obtained from the same cell line have a consistent genetic background. Therefore, the use of somatic cell nuclear transfer technology to construct genetically modified non-human primate models can solve all the problems as mentioned above. At present, the genetically modified non-human primate models that the present invention has been developing using this technology include:

1. Using somatic cell nuclear transfer technology to construct a precise gene knock-in model of cynomolgus/rhesus monkey:
   (1) Knocking in the green fluorescent protein at AAVS1 site: AAVS1-GFP Knock In.
   (2) Knocking in the cre sequence at the AAVS1 site: AAVS1-Cre Knock In.
   (3) Knocking in the LSL-CHR2 sequence at the AAVS1 site: AAVS1-LSL-CHR2 Knock In.
   (4) Knocking in the light-sensitive ion channel protein CHR2 at CamkIIa site: CamkIIa-CHR2-EYFP Knock In.
   (5) Knocking in calcium imaging protein Gcamp6s at CamkIIa site: CamkIIa-Gcamp6s Knock In.
   (6) Knocking in cre sequence at CamkIIa site: CamkIIa-Cre Knock In.
   (7) Knocking in the light-sensitive ion channel protein CHR2 at Vgat site: Vgat-CHR2-EYFP Knock In.
   (8) Knocking in calcium imaging protein Gcamp6s at Vgat site: Vgat-Gcamp6s Knock In.
   (9) Knocking in the cre sequence at the Vgat site: Vgat-Cre Knock In.
   (10) Knocking in cre sequence at Chat (Choline acetyltransferase) site: Chat-Cre Knock in
   (11) Knocking in Chr2 sequence at Chat site: Chat-CHR2-EFYP Knock in
   (12) Knocking in Gcamp6s sequence at Chat site: Chat-gcamp6s Knock in
   (13) Knocking in the cre sequence at Drd1 (Dopamine receptor DO: Drd1-Cre Knock In
   (14) Knocking in Chr2 sequence at Drd1: Drd1-Chr2-EYFP Knock In
   (15) Knocking in the cre sequence at Drd2 (Dopamine receptor D2): Drd2-Cre Knock In
   (16) Knocking in Chr2 sequence at Drd2: Drd2-Chr2-EYFP Knock In
   (17) Knocking in Chr2 sequence at GFAP site: GFAP-CHR2-EFYP Knock in
   (18) Knocking in the cre sequence at the GFAP site: GFAP-Cre Knock in
   (19) Knocking in gcamp6s sequence at GFAP site: GFAP-gcamp6s Knock in
   (20) Knocking in cre sequence at TH (hydroxytryptamine) site: TH-Cre Knock In
   (21) Knocking in Chr2 sequence at TH site: TH-Chr2-EYFP Knock In
   (22) Knocking in the cre sequence at Nestin site: Nestin-Cre Knock In
   (23) Knocking in genes specific to other tissues or cells;
2. Using somatic cell nuclear transfer technology to construct a cynomolgus/rhesus monkey point mutation model:
   (1) SOD1 A4V point mutation
   (2) SOD1 H46R point mutation
   (3) SOD1 G93A point mutation
   (4) Foxp2 T327N+N349S point mutation
3. Use somatic cell nuclear transfer technology to clone multiple cynomolgus monkey/rhesus monkey gene knockout disease or developmental disorder models with the consistent genetic background:
   (1) Cloning a PRRT2 knockout monkey model with consistent genetic background.
   (2) Cloning the FMR1 knockout monkey model with the consistent genetic background.
   (3) Cloning the ASPM knockout monkey model with consistent genetic background.
   (4) Cloning a DISC1 knockout monkey model with consistent genetic background.
   (5) Cloning the MKRN3 knockout monkey model with consistent genetic background.
   (6) Cloning the SNCA knockout monkey model with consistent genetic background.
   (7) Cloning the LRRK2 knockout monkey model with consistent genetic background.
   (8) Clone GBA knockout monkey model with consistent genetic background.
   (9) Cloning a PRKN knockout monkey model with consistent genetic background.
   (10) Cloning a PINK1 knockout monkey model with consistent genetic background.
   (11) Cloning a PARK7 knockout monkey model with consistent genetic background.
   (12) Cloning a VPS35 knockout monkey model with consistent genetic background.
   (13) Cloning the EIF4G1 knockout monkey model with the consistent genetic background.
   (14) Cloning a Bmal1 knockout monkey model with consistent genetic background.
   (15) Cloning the LRRK2+PINK1+PARK7 gene knockout monkey model with the consistent genetic background.
4. Using somatic cell nuclear transfer technology to clone multiple transgenes and gene knockout cynomolgus monkey/rhesus monkey models with the consistent genetic background for research on Alzheimer's disease, Parkinson's disease, amyotrophic lateral sclerosis, autism, depression, Huntington's syndrome and other diseases.

Example 12 Preparation of BMAL1 Gene Knockout Cynomolgus Monkey Somatic Cells

ARNT-Like 1 (BMAL1) is a transcription factor that regulates the circadian rhythm. In the present invention, 5 cynomolgus monkeys with BMAL1 gene editing were obtained using CRISPR/Cas9 method. Among them, monkey A6 was selected as the donor cell source monkey for cloning, because the expression of BMAL1 protein was not detected in this monkey, and it showed obvious physiological disease phenotypes, including the physiological circulation inhibition of blood hormones, frequent night activities, and reduced rapid eye movement (REM) and non-rapid eye movement sleep periods, and psychosis-related behaviors. Therefore, skin fibroblasts from A6 monkey were taken and cultured and used for SCNT (FIG. 9, A-C).

The karyotype of the cultured fibroblasts showed a normal diploid with 42 chromosomes (FIG. 9D). Genotype analysis was performed on the ear tip tissue, blood cells and fibroblasts of A6 monkeys. Through monoclonal sequencing of PCR products, two types of BMAL1 mutations were found: "−8 bp" and "−8 bp, +4 bp, 2 bpPM" (FIG. 9E). Then, the genotype analysis of single fibroblasts showed that there was a homozygous mutation of "−8 bp/−8 bp" or a heterozygous mutation of "−8 bp/−8 bp, +4 bp, 2 bpPM" in the BMAL1 gene (FIG. 9F).

1. Using Fibroblasts from BMAL1-Edited Monkey for SCNT

SCNT was performed using fibroblasts derived from BMAL1 gene-edited rhesus monkey A6. By superovulating female macaques, mature oocytes were obtained. Then, Sendai virus was used to assist the fusion of single fibroblasts with enucleated oocytes to obtain SCNT oocytes, and incubated with calcium ionophores and 6-dimethylamine. In order to promote epigenetic reprogramming after nuclear transfer, SCNT embryos were incubated with histone deacetylase inhibitor trichostatin (TSA), and H3K9me3 demethylation factor Kdm4d mRNA was injected at the same time (FIG. 10 A, B). It was found that using fibroblasts from BMAL1 gene-edited monkey A6 for SCNT, a higher proportion of blastocyst formation was obtained (10/17, 58.8%). Among these blastocysts, 80% (8/10) forms a distinct inner cell mass (ICM), which is a sign of normal embryonic development. Due to the high efficiency of blastocyst formation and ICM formation, we transferred 325 SCNT embryos in the early developmental stage (2-8 cells) to 65 surrogate mother monkeys, of which 16 female monkeys were pregnant. In the end, 5 surviving cloned monkey individuals (B1-B5) were obtained, all of which are now alive under artificial feeding (currently 51-141 days) (FIG. 10C, Table 1). The relationship between the number of passages of fibroblast culture and cloning efficiency in SCNT was also studied. As shown in Table 1, after 4 passages of fibroblasts undergoing SCNT, the recipient monkey's pregnancy rate and live birth rate were the best, indicating that the success rate of cloning may be related to the number of passages of donor cell culture.

TABLE 1

Statistics of SCNT embryos of BMAL1 gene-edited fibroblasts

| Cell generation | Embryo transfer (pieces) | Transplant recipient (number) | Pregnancy recipient (number) | Number of births (numbering) |
|---|---|---|---|---|
| 2nd generation | 118 | 23 | 7 | 1 (B1) |
| 3rd generation | 148 | 30 | 4 | 1 (B2) |
| 4th generation | 59 | 12 | 5 | 3 (B3, B4, B5) |
| total | 325 | 65 | 16 | 5 |

2. Genotype Analysis of Cloned Monkey

First, the ear tip tissues of 5 cloned monkeys were analyzed for BMAL1 genotype. It was found that 4 cloned monkeys (B1, B3, B4, B5) carried homozygous mutations of the BMAL1 gene ("−8 bp/−8 bp, +4 bp, 2 bpPM"), and 1 monkey (B2) a heterozygous mutation of the BMAL1 gene ("−8 bp/−8 bp") (FIG. 10D). This was the same as the mutant genotype of the donor fibroblasts and the mutant genotype of monkey A6 tested previously.

To determine the genetic origin of cloned monkeys, single nucleotide polymorphisms of mitochondrial DNA (mtDNA) and short tandem repeats of nuclear DNA were analyzed. It was found that the ND3 gene of the mitochondrial DNA in cloned monkey was the same as the respective oocyte donor monkeys, but different from the recipient monkey and the donor fibroblasts (FIG. 11 A-E). STR analysis of 29 sites showed that the donor fibroblasts of 5 cloned monkeys had the same nuclear DNA as monkey A6, but different from the nuclear DNA of recipient monkeys and oocyte donor monkeys (FIG. 11F).

Although whole-genome sequencing and PCR analysis confirmed that there is no off-target phenomenon in BMAL1 gene-edited monkey A6, off-target analysis was performed on the genomic DNA of the ear tissues of 5 cloned monkeys. No mutation was found at the predicted potential off-target site. In addition, wild-type BMAL1 transcripts were not detected in the blood of B1 cloned monkeys (the remaining 4 clones had not yet reached the age for blood collection). (FIG. 11G).

DISCUSSION

The invention knocked out the important rhythm-related gene BMAL1 in the genome of the cynomolgus monkey through the CRISPR/Cas9 system, and obtained 5 gene-edited monkeys. In this study, fibroblasts isolated from one of the obvious monkey skins were served as somatic cell nuclear donors, and 5 BMAL1 gene-edited cloned monkeys were successfully obtained. The sequence alignment, microsatellite analysis and mitochondrial DNA comparison of the first monkeys and cloned monkeys showed that these cloned monkeys and the first monkeys had the same genetic background. These results indicate that the cynomolgus monkey disease model edited by CRISPR/Cas9 can be used as a donor for nuclear transfer to obtain cloned monkeys with consistent genetic background, which provides a favorable prospect for related disease research and model construction.

In previous research, the applicant used fibroblasts from an aborted female fetal monkey as a nuclear donor, and successfully cloned "Zhongzhong" and "Huahua". The difference is that in this experiment, fibroblasts isolated from the skin of a 16-month-old immature monkey demonstrated the feasibility of male cells as nuclear donors for the first time. Although the current cloning efficiency is still low, we will further optimize the culture conditions of fibroblasts. For example, it is found that the cloning efficiency of fibroblasts after several passages will be higher than that of primary cells. In addition, Kdm4d, as the demethylase of H3K9me3, can significantly improve the efficiency of reprogramming in mice and monkeys by removing the reprogrammed methylation regions in nuclear transfer embryos; Xist-mediated X chromosome silencing is likely to likely to be conserved in mice, pigs, and primates. In addition, DNA remethylation and deletion of H3K27me3 may also be key factors affecting cloning efficiency.

In theory, the positive cells obtained after in vitro gene editing and screening are the most ideal choice as nuclear donors. In this experiment, the applicant used cells isolated from adult editing monkeys. Because the BMAL1 gene of this first monkey was completely knocked out and showed a phenotype similar to human discipline disorder, it was selected as the source of a nuclear donor. After testing, it was found that the first monkeys had two main genotypes, namely 8 bp homozygous knockout ("−8 bp/−8 bp") and heterozygous 8 bp knockout, 4 bp knock-in and 2 bp point mutation ("−8 bp/−8 bp, +4 bp, 2 bpPM"). Each of these 5 cloned monkeys had only one genotype, indicating that this chimerism phenomenon does not appear in these 5 cloned monkeys. Therefore, the present invention believes that the current cloning method is very mature, and the phenotype of these cloned monkeys will also be further analyzed.

All documents mentioned in the present invention are cited as references in this application, as if each document was individually cited as a reference. In addition, it should be understood that after reading the above teaching content of the present invention, those skilled in the art can make various changes or modifications to the present invention, and these equivalent forms also fall within the scope defined by the appended claims of the present application.

The invention claimed is:

1. A method for preparing a non-human primate somatic cell cloned animal, comprising the steps:
  (i) providing a reconstructed oocyte, which is from the non-human primate, wherein the reconstructed oocyte is at a one-cell stage;
  (ii) performing an activation treatment on the reconstructed oocyte to obtain an activated reconstructed oocyte;
  (iii) performing a reprogramming treatment to for (a) the activated reconstructed oocyte to obtain a reprogrammed reconstructed embryo; and
  (iv) regenerating the reprogrammed reconstructed embryo to obtain a non-human primate somatic cell cloned animal,
  wherein:
    in step (ii), the activation treatment is performed with an electrical stimulation and an activation treatment agent comprising the combination of a calcium ion activator, a histone deacetylase inhibitor, dimethylaminopyridine (6-DMAP), and puromycin;
    in step (iii), the reprogramming treatment is performed with a reprogramming activator comprising an mRNA encoding a Kdm4d protein, wherein the mRNA is injected to the activated reconstructed oocyte at 5-6 hours post activation; and
    in step (iv), the "regenerating" is performed in a uterus of a non-human primate surrogate animal.

2. The method of claim 1, wherein $10^2$-$10^8$ copies/cell of mRNA encoding Kdm4d protein are injected into the activated reconstructed oocyte.

3. The method of claim 1, wherein the step (iv) includes:
  (iv1) culturing the reprogrammed reconstructed oocyte in vitro or in vivo to form a reconstructed embryo; and
  (iv2) transplanting the reconstructed embryo into the oviduct of a non-human primate, thereby obtaining a somatic cloned animal of the non-human primate.

4. The method of claim 2, wherein $10^4$-$10^6$ copies/cell of the mRNA encoding the Kdm4d protein are injected into the activated reconstructed oocyte.

* * * * *